(12) United States Patent
Siegal et al.

(10) Patent No.: US 8,986,388 B2
(45) Date of Patent: Mar. 24, 2015

(54) SURGICAL SYSTEMS AND METHODS FOR IMPLANTING DEFLECTABLE IMPLANTS

(75) Inventors: Tzony Siegal, Shoeva (IL); Oded Loebl, Tel Mond (IL); Didier Toubia, Raanana (IL)

(73) Assignee: N.L.T. Spine Ltd., Kfar Saba (IL)

( * ) Notice: Subject to any disclaimer, the term of this patent is extended or adjusted under 35 U.S.C. 154(b) by 0 days.

(21) Appl. No.: 13/810,225

(22) PCT Filed: Jul. 14, 2011

(86) PCT No.: PCT/IB2011/053143
§ 371 (c)(1),
(2), (4) Date: Jan. 15, 2013

(87) PCT Pub. No.: WO2012/007918
PCT Pub. Date: Jan. 19, 2012

(65) Prior Publication Data
US 2013/0144391 A1 Jun. 6, 2013

Related U.S. Application Data

(60) Provisional application No. 61/364,412, filed on Jul. 15, 2010.

(51) Int. Cl.
*A61F 2/44* (2006.01)
*A61F 2/46* (2006.01)
(Continued)

(52) U.S. Cl.
CPC .............. *A61F 2/4465* (2013.01); *A61F 2/442* (2013.01); *A61F 2/4455* (2013.01); *A61F 2/4611* (2013.01); *A61F 2/30965* (2013.01);
(Continued)

(58) Field of Classification Search
CPC .................. A61F 2/4425; A61F 2002/30116; A61F 2002/30121; A61F 2002/30123
USPC ............................................. 623/17.11–17.16
See application file for complete search history.

(56) References Cited

U.S. PATENT DOCUMENTS 5,059,193 A * 10/1991 Kuslich ........................ 606/247
5,390,683 A * 2/1995 Pisharodi ....................... 128/898
(Continued)

FOREIGN PATENT DOCUMENTS

WO WO 2008084479 A2 * 7/2008 ................ A61F 2/44
WO 2009073918 6/2009

*Primary Examiner* — Eduardo C Robert
*Assistant Examiner* — Jacqueline Johanas
(74) *Attorney, Agent, or Firm* — Mark M Friedman

(57) ABSTRACT

Deflectable implants, systems and methods for implanting deflectable implants are disclosed. The deflectable implant (100) includes at least one sequence of segments (102), the sequence includes at least two segments (102), the segments (102) being interconnected at effective hinges (107), the sequence assuming a straightened or low curvature insertion state for insertion into the body, the sequence being deflectable to a fully deflected state defined by abutment of abutment features of adjacent of the segments (102). The deflectable implant (100) includes further a linkage mechanically linked to at least part of at least one of the sequences of segments (102) for deflecting the at least one sequence of segments (102) from the insertion state towards the fully deflected state wherein the at least one sequence is at least part of a loop structure assuming a low profile folded state with the at least one sequence towards the fully deflected state generates an open state of the loop structure and wherein the loop defines an enclosed volume (106).

11 Claims, 23 Drawing Sheets

(51) Int. Cl.
  *A61F 2/30*       (2006.01)
  *A61F 2/28*       (2006.01)
(52) U.S. Cl.
  CPC ............... *A61F 2/44* (2013.01); *A61F 2/4601*
      (2013.01); *A61F 2002/2817* (2013.01); *A61F*
          *2002/2835* (2013.01); *A61F 2002/30126*
      (2013.01); *A61F 2002/30179* (2013.01); *A61F*
          *2002/302* (2013.01); *A61F 2002/30471*
          (2013.01); *A61F 2002/305* (2013.01); *A61F*
          *2002/30579* (2013.01); *A61F 2002/4415*
      (2013.01); *A61F 2002/4475* (2013.01); *A61F*
          *2002/4635* (2013.01); *A61F 2210/0019*
      (2013.01); *A61F 2220/0025* (2013.01); *A61F*
          *2220/0091* (2013.01); *A61F 2230/0008*
          (2013.01); *A61F 2230/0065* (2013.01); *A61F*
          *2310/00017* (2013.01); *A61F 2310/00023*
                                                   (2013.01)
  USPC ..................................................... 623/17.16

(56) References Cited

U.S. PATENT DOCUMENTS

| | | | | |
|---|---|---|---|---|
| 6,039,761 | A * | 3/2000 | Li et al. | 623/17.16 |
| 6,126,689 | A * | 10/2000 | Brett | 623/17.16 |
| 6,190,414 | B1 | 2/2001 | Young et al. | |
| 6,332,894 | B1 * | 12/2001 | Stalcup et al. | 623/17.11 |
| 6,375,682 | B1 | 4/2002 | Fleischmann et al. | |
| 6,419,705 | B1 | 7/2002 | Erickson | |
| 6,620,196 | B1 * | 9/2003 | Trieu | 623/17.16 |
| 6,676,665 | B2 * | 1/2004 | Foley et al. | 606/105 |
| 6,830,589 | B2 | 12/2004 | Erickson | |
| 7,087,055 | B2 | 8/2006 | Lim et al. | |
| 7,097,648 | B1 | 8/2006 | Globerman et al. | |
| 7,220,282 | B2 * | 5/2007 | Kuslich et al. | 623/17.16 |
| 7,625,377 | B2 * | 12/2009 | Veldhuizen et al. | 606/90 |
| 7,763,074 | B2 * | 7/2010 | Altarac et al. | 623/17.11 |
| 7,799,081 | B2 | 9/2010 | McKinley | |
| 7,846,206 | B2 * | 12/2010 | Oglaza et al. | 623/17.11 |
| 7,901,409 | B2 * | 3/2011 | Canaveral et al. | 606/86 R |
| 7,905,920 | B2 * | 3/2011 | Galea | 623/17.11 |
| 7,909,872 | B2 * | 3/2011 | Zipnick et al. | 623/17.11 |
| 7,938,860 | B2 * | 5/2011 | Trieu | 623/17.16 |
| 7,947,078 | B2 | 5/2011 | Siegal | |
| 7,959,652 | B2 | 6/2011 | Zucherman et al. | |
| 8,021,429 | B2 | 9/2011 | Viker | |
| 8,025,697 | B2 | 9/2011 | McClellan, III et al. | |
| 8,062,375 | B2 | 11/2011 | Glerum et al. | |
| 8,197,548 | B2 | 6/2012 | Sack et al. | |
| 8,292,963 | B2 | 10/2012 | Miller et al. | |
| 8,303,658 | B2 | 11/2012 | Peterman | |
| 8,317,798 | B2 | 11/2012 | Lim et al. | |
| 8,317,802 | B1 | 11/2012 | Manzi et al. | |
| 8,317,866 | B2 | 11/2012 | Palmatier et al. | |
| 8,337,531 | B2 | 12/2012 | Johnson et al. | |
| 8,343,193 | B2 | 1/2013 | Johnson et al. | |
| 8,349,013 | B2 | 1/2013 | Zucherman et al. | |
| 8,349,014 | B2 | 1/2013 | Barreiro et al. | |
| 8,398,713 | B2 | 3/2013 | Weiman | |
| 2003/0236520 | A1 * | 12/2003 | Lim et al. | 606/61 |
| 2004/0059418 | A1 * | 3/2004 | McKay et al. | 623/17.16 |
| 2004/0193158 | A1 * | 9/2004 | Lim et al. | 606/61 |
| 2005/0113920 | A1 * | 5/2005 | Foley et al. | 623/17.11 |
| 2005/0143827 | A1 * | 6/2005 | Globerman et al. | 623/17.16 |
| 2005/0182416 | A1 * | 8/2005 | Lim et al. | 606/90 |
| 2005/0228391 | A1 * | 10/2005 | Levy et al. | 606/86 |
| 2006/0004455 | A1 * | 1/2006 | Leonard et al. | 623/17.15 |
| 2006/0041258 | A1 * | 2/2006 | Galea | 606/61 |
| 2006/0085070 | A1 * | 4/2006 | Kim | 623/17.11 |
| 2006/0142858 | A1 * | 6/2006 | Colleran et al. | 623/17.11 |
| 2006/0224241 | A1 * | 10/2006 | Butler et al. | 623/17.15 |
| 2007/0032791 | A1 * | 2/2007 | Greenhalgh | 606/61 |
| 2007/0123986 | A1 * | 5/2007 | Schaller | 623/17.11 |
| 2007/0173939 | A1 * | 7/2007 | Kim et al. | 623/17.11 |
| 2007/0233245 | A1 * | 10/2007 | Trieu | 623/17.11 |
| 2008/0243255 | A1 * | 10/2008 | Butler et al. | 623/17.16 |
| 2008/0312743 | A1 * | 12/2008 | Vila et al. | 623/17.16 |
| 2009/0216274 | A1 * | 8/2009 | Morancy-Meister et al. | 606/247 |
| 2009/0240334 | A1 | 9/2009 | Richelsoph | |
| 2009/0270873 | A1 * | 10/2009 | Fabian | 606/99 |
| 2010/0286787 | A1 * | 11/2010 | Villiers et al. | 623/17.16 |
| 2011/0319997 | A1 | 12/2011 | Glerum et al. | |
| 2012/0004732 | A1 * | 1/2012 | Goel et al. | 623/17.16 |
| 2012/0083889 | A1 * | 4/2012 | Purcell et al. | 623/17.16 |
| 2012/0123546 | A1 | 5/2012 | Medina | |
| 2012/0209386 | A1 * | 8/2012 | Triplett et al. | 623/17.16 |
| 2013/0041471 | A1 * | 2/2013 | Siegal et al. | 623/17.16 |
| 2013/0079883 | A1 * | 3/2013 | Butler et al. | 623/17.16 |
| 2013/0110239 | A1 * | 5/2013 | Siegal et al. | 623/17.16 |
| 2013/0304214 | A1 * | 11/2013 | Siegal et al. | 623/17.16 |
| 2014/0074096 | A1 | 3/2014 | Siegal et al. | 606/79 |

* cited by examiner

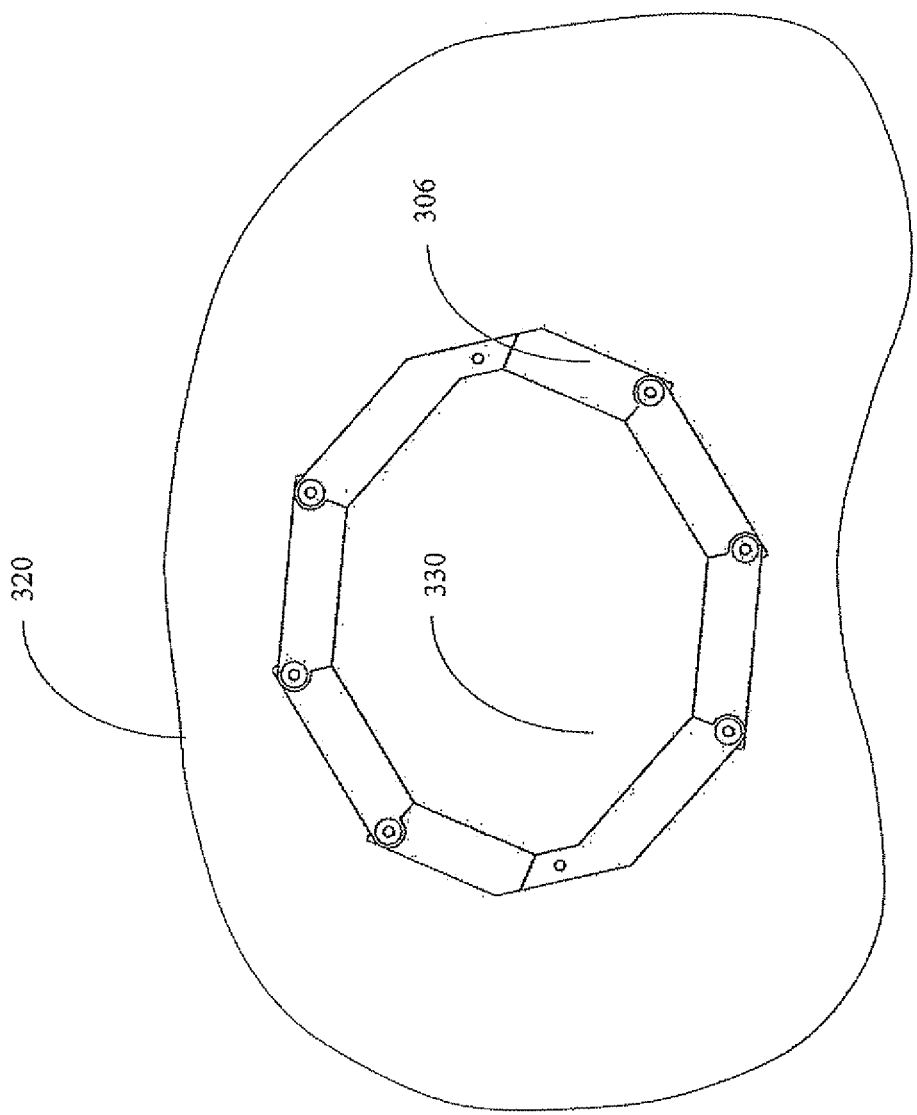

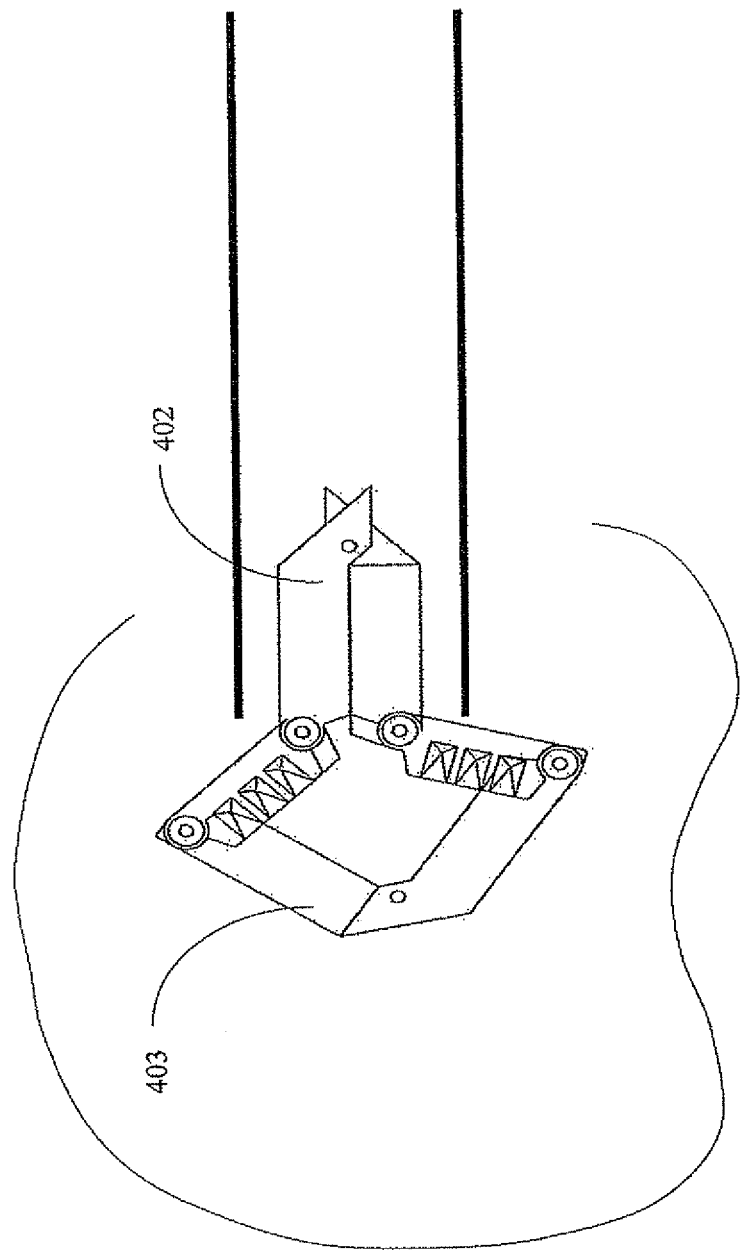

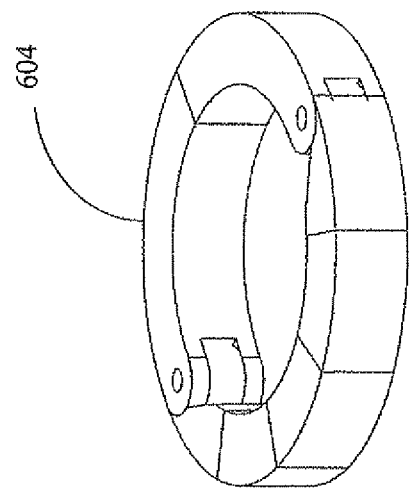
FIG. 6A(2)
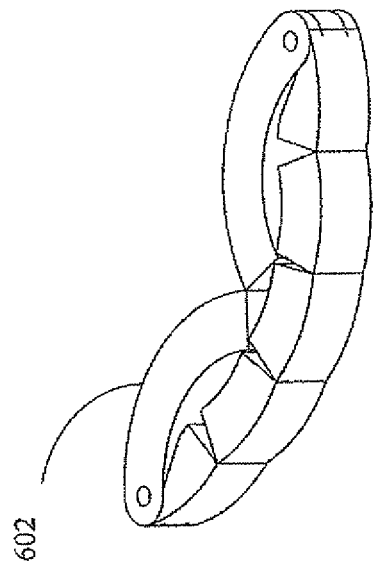
FIG. 6A(1)

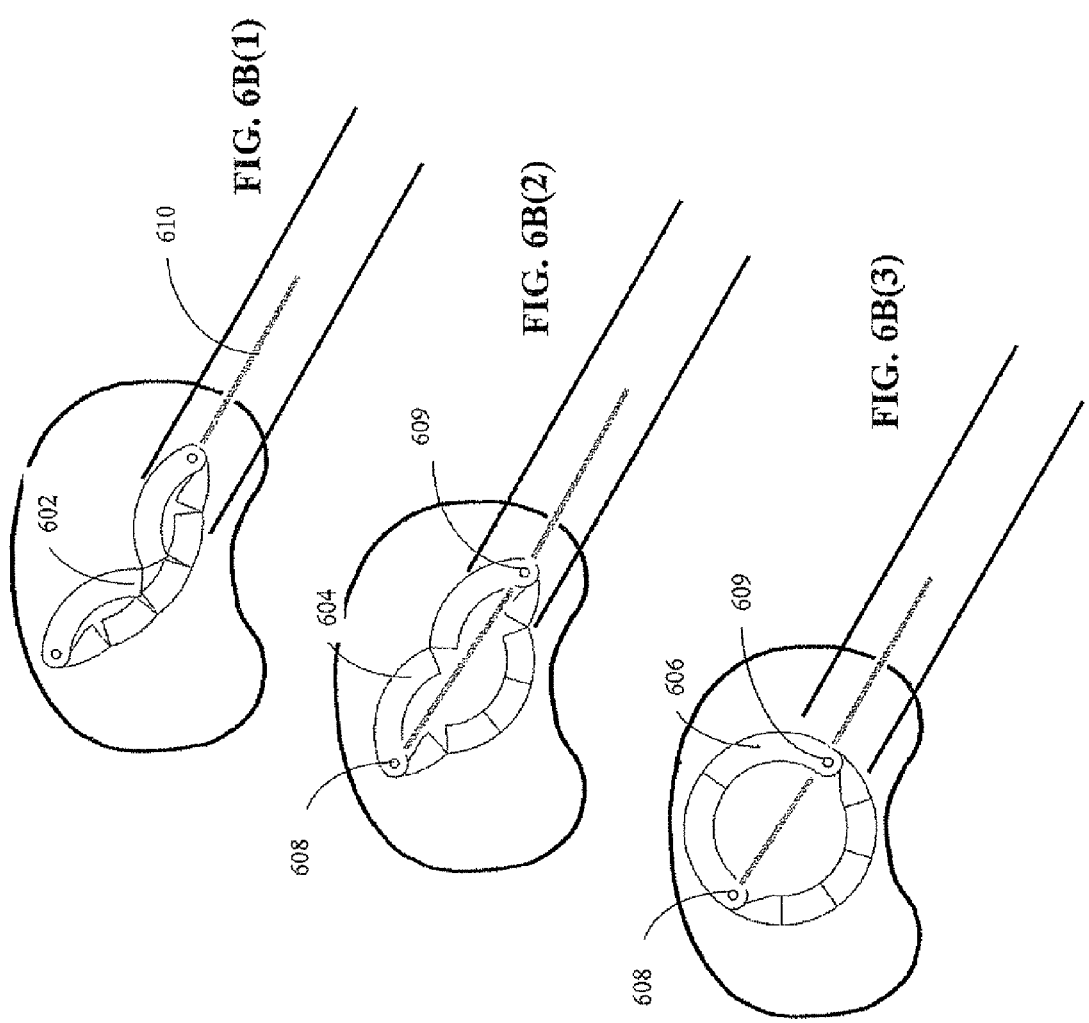

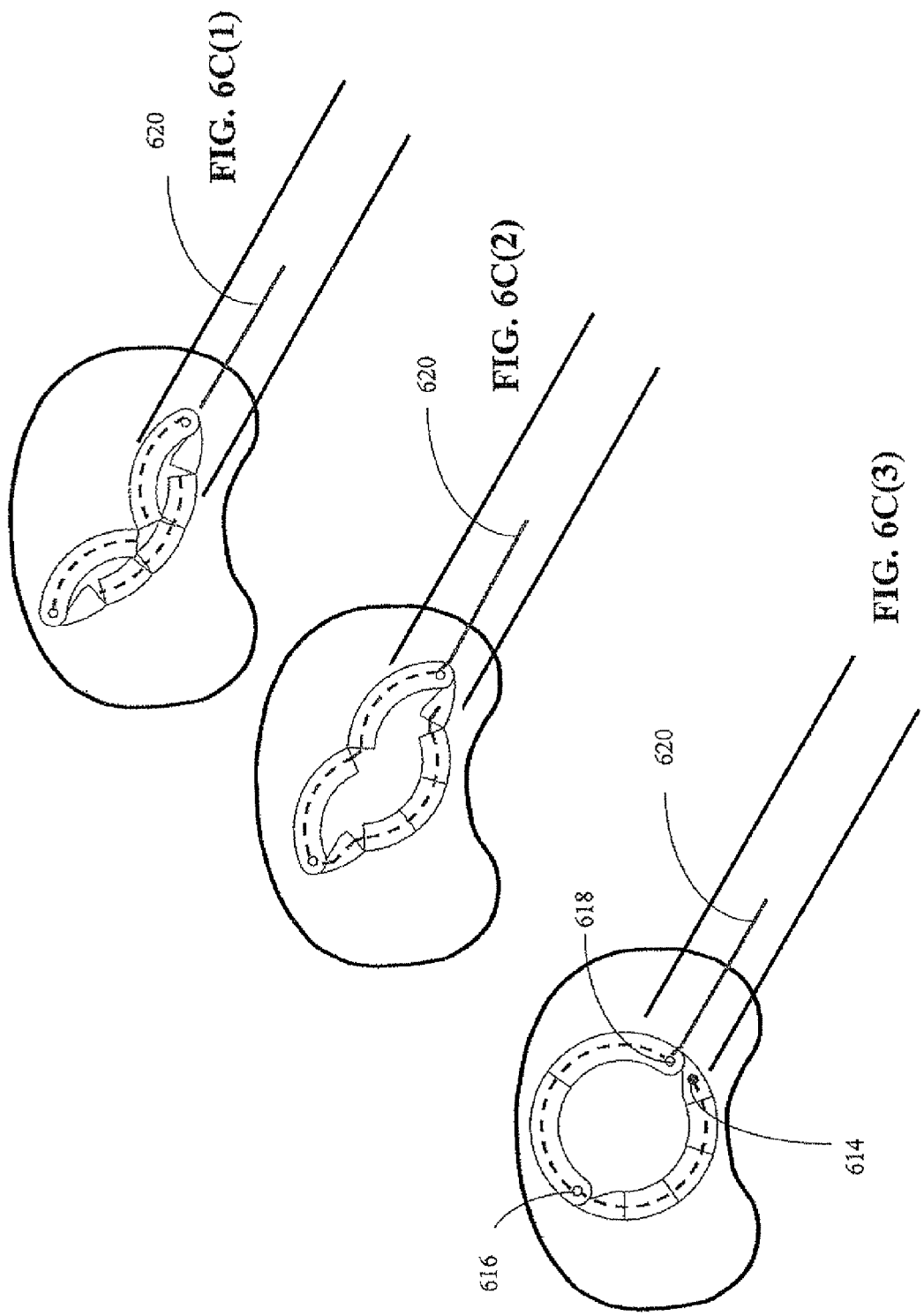

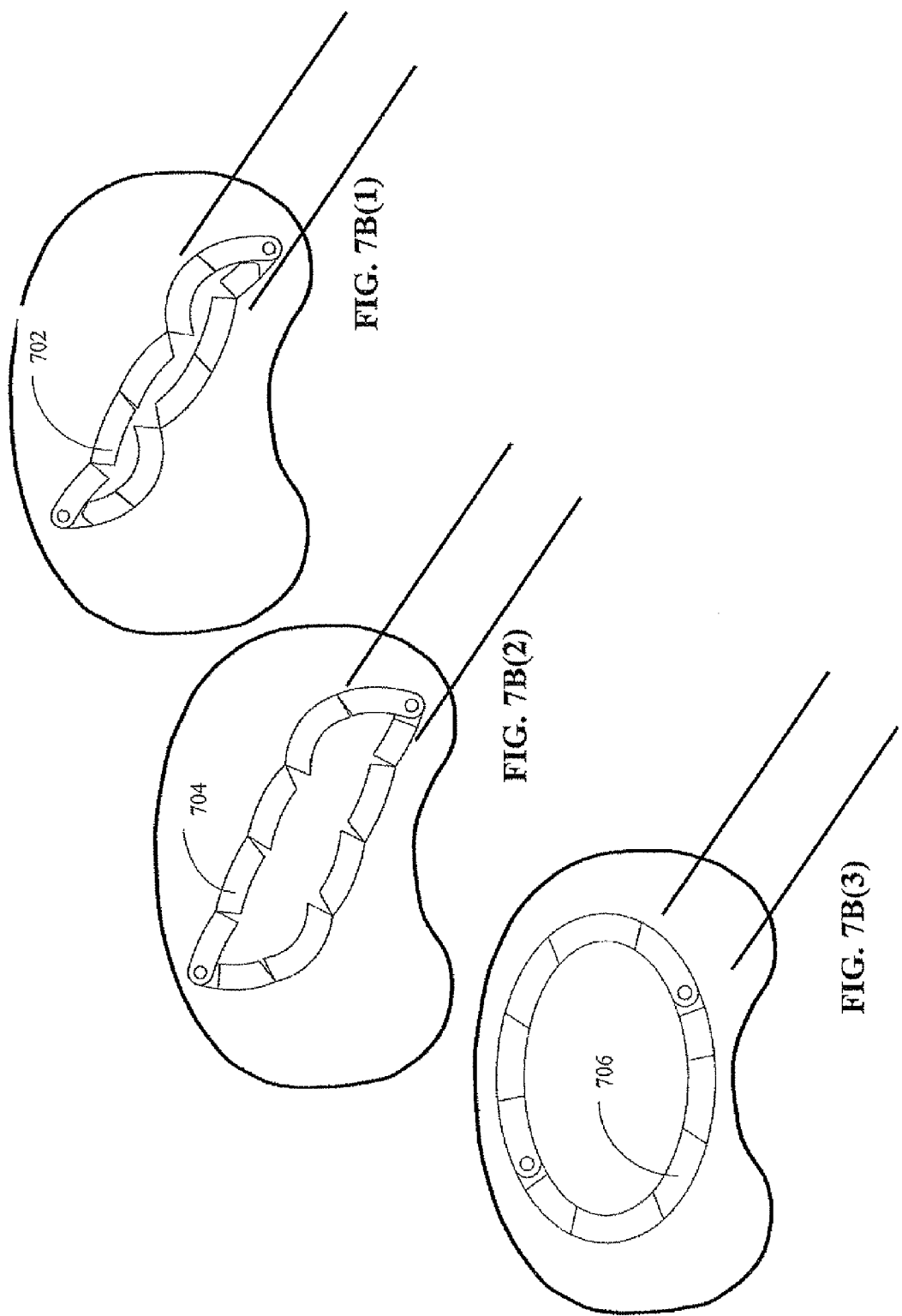

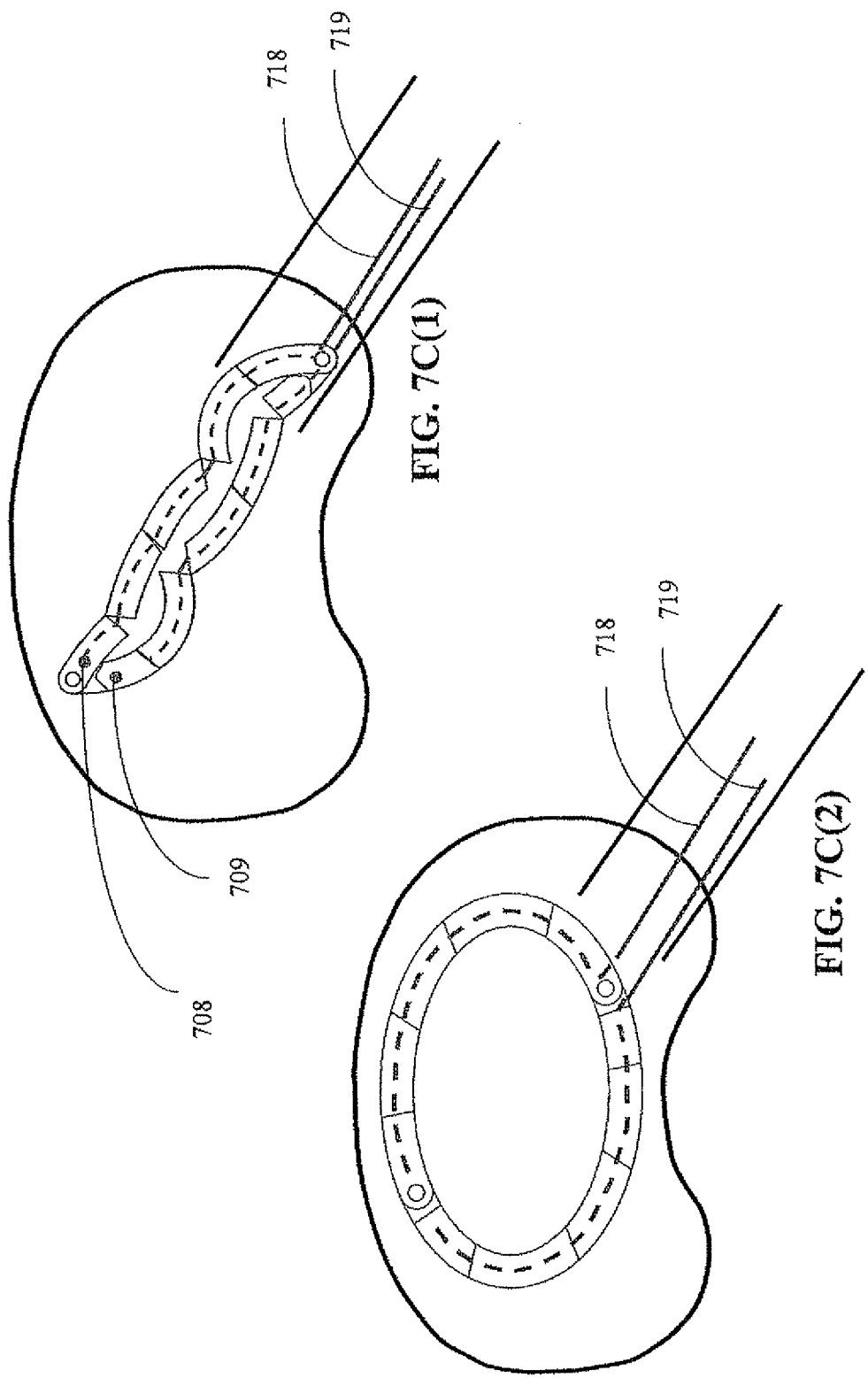

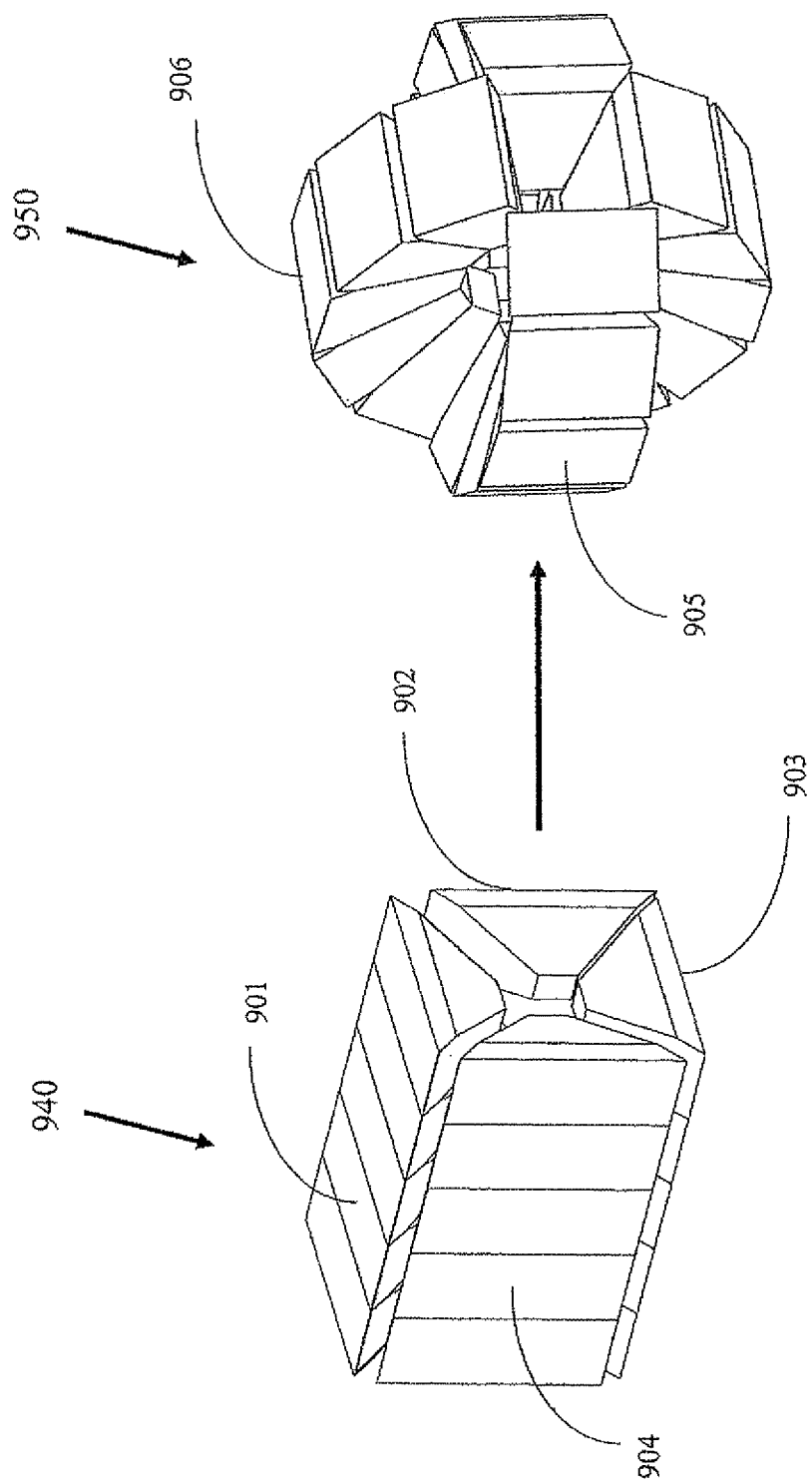
FIG. 9A(1)    FIG. 9A(2)

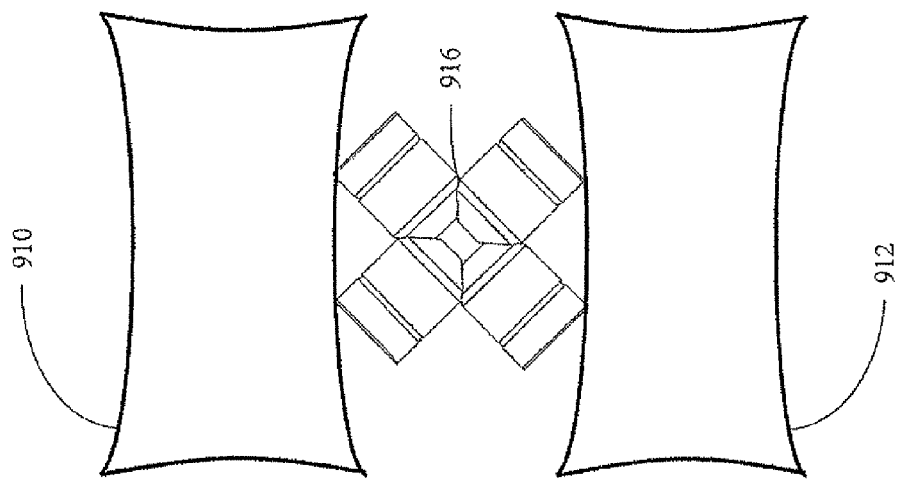
FIG. 9B(2)
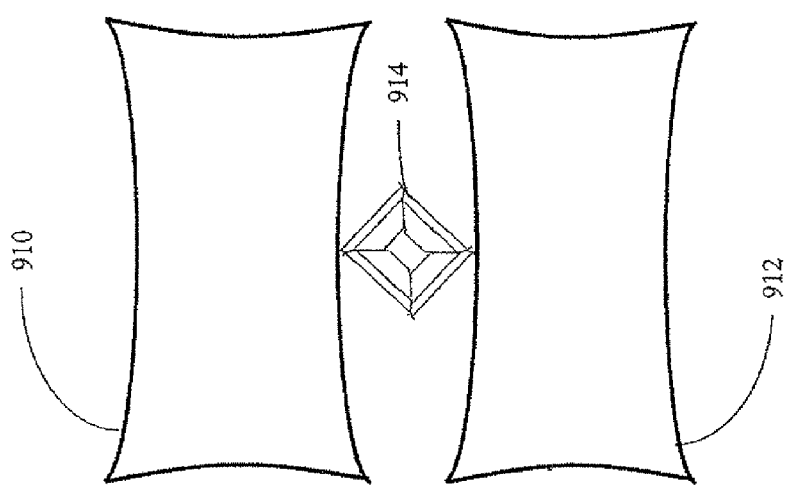
FIG. 9B(1)

SURGICAL SYSTEMS AND METHODS FOR IMPLANTING DEFLECTABLE IMPLANTS

FIELD OF THE INVENTION

The invention relates generally to implants, and more particularly to systems and methods for implanting deflectable implants.

BACKGROUND OF THE INVENTION

Minimally invasive subcutaneous procedures, which are performed through a small orifice in the skin, limit the size of the surgery tools and implants that are used.

Hence it would be highly advantageous to develop implants that have small cross sections such that they can be inserted easily through a small orifice in the skin and be deflected into their final functional expanded shape at the intended implantation site in the body.

It would be highly advantageous to provide implants for spinal surgeries such as interbody fusion, motion preservation and vertebral augmentation that may be inserted into the body in minimally invasive procedures.

SUMMARY OF THE INVENTION

Embodiments of the present invention disclose deflectable implants, systems and methods for implanting deflectable implants. The deflectable implant includes at least one sequence of segments, the sequence includes at least two segments, the segments being interconnected at effective hinges, the sequence assuming a straightened or low curvature insertion state for insertion into the body, the sequence being deflectable to a fully deflected state at least partially defined by abutment of abutment features of adjacent of the segments. The at least one sequence is at least part of a loop structure assuming a low profile folded state with the at least one sequence in the insertion state, and wherein deflection of the at least one sequence towards the fully deflected state generates an open state of the loop structure in which the loop at least partially defines an enclosed volume.

According to a further feature of an embodiment of the present invention, the implant includes at least two of the sequences of segments, the at least two sequences of segments being hingedly interconnected at both a distal end and a proximal end of each sequence.

According to a further feature of an embodiment of the present invention, the hinged interconnection is configured to allow closing together of the two sequences of segments.

According to a further feature of an embodiment of the present invention, there is also provided a linkage mechanically linked to at least part of at least one of the sequences of segments for deflecting the at least one sequence of segments from the insertion state towards the fully deflected state.

According to a further feature of an embodiment of the present invention, the linkage includes a tensioning element deployable to selectively reduce a distance between the distal and proximal ends of the sequences.

According to a further feature of an embodiment of the present invention, the linkage includes a tensioning element extending along at least one of the sequences to allow selective deflection of the sequence.

According to a further feature of an embodiment of the present invention, the at least one sequence is resiliently biased towards the fully deflected state, and is temporarily deformed to the insertion state.

According to a further feature of an embodiment of the present invention, the implant includes further at least one opening in the sequence of segments to allow access to the enclosed volume in the loop.

According to a further feature of an embodiment of the present invention, an implant including, a single body of flexible material implant, including at least first and second elongated sides interconnected at their proximal and distal ends, the at least first and second elongated interconnected sides assuming a straightened insertion state for insertion into a body, the at least first and second elongated interconnected sides being deflectable to a fully deflected loop inside the body, the loop defining an enclosed volume. The implant further including a linkage mechanically linked to at least part of at least one of the elongated interconnected sides for deflecting the at least first and second elongated interconnected sides from the straightened insertion state towards the fully deflected loop inside the body, wherein the implant assumes a low cross section profile in its straightened insertion state.

According to a further feature of an embodiment of the present invention, an implant for interbody fusion is disclosed. The implant including (a) a straightened insertion state for insertion into a body and a fully deflected loop state inside the body, the loop defining an enclosed volume, (b) at least one opening in the deflected state allowing access to the enclosed volume, (c) a linkage for deflecting the implant from the straightened insertion state towards the fully deflected loop inside the body, wherein the implant assumes a low cross section profile in its straightened insertion state, and wherein the at least one opening allows filling of the enclosed volume in the fully deflected loop state with filling material for interbody fusion.

According to a further feature of an embodiment of the present invention, an implant for motion preservation is disclosed. The implant including (a) a straightened insertion state for insertion into a body and a fully deflected loop state inside the body, the loop defining an enclosed volume, (b) at least one opening in the deflected state allowing access to the enclosed volume, (c) a linkage for deflecting the implant from the straightened insertion state towards the fully deflected loop inside the body, wherein the implant assumes a low cross section profile in its straightened insertion state and wherein the at least one opening is used to fill the enclosed volume in the fully deflected loop state with inert filling material for motion preservation.

According to a further feature of an embodiment of the present invention, an implanting system is disclosed. The implanting system including further an elongated conduit for inserting the implant in the straightened insertion state into the body.

According to a further feature of an embodiment of the present invention, an implanting system is disclosed. The implanting system including further an elongated guide for loading on the tip of the guide the straightened state implant and press-fitting the implant into the body.

According to a further feature of an embodiment of the present invention, the at least first and second elongated interconnected sides are made of one elongated segment having slits along the elongated side and wherein the slits are closed in the fully deflected loop state.

According to a further feature of an embodiment of the present invention, the fully deflected loop shape is selected from the group consisting of: toroidal polyhedrons, ring toroids, oval toroids and multi-ring toroids.

According to a further feature of an embodiment of the present invention, the linkage used to deflect the implant to its fully deflected state comprises at least one tensioning element deployable to selectively reduce a distance between the distal and proximal ends.

According to a further feature of an embodiment of the present invention, the tensioning element extending along at least one of the elongated interconnected sides to allow selective deflection of the elongated side towards the implant fully deflected state.

According to a further feature of an embodiment of the present invention, the linkage used to deflect the implant towards its fully deflected state is selected from the group consisting of: inflation balloons, springs, memory-shape materials, threaded rods and jacking mechanisms.

According to a further feature of an embodiment of the present invention, the implant is an intervertebral implant and/or intravertebral implant.

According to a further feature of an embodiment of the present invention, an implant system is disclosed. The implant system includes an injector containing filling material selected from the group consisting of biocompatible materials, bone grafts, bone chips, bone-growth enhancing agents for interbody fusion and inert filling materials such as cements for motion preservation.

According to a further feature of an embodiment of the present invention, the implants are made primarily from material selected from the group consisting of polymers such as Poly Ethylene, Ultra High Molecular Weight Poly Ethylene, Poly Ether Ether Ketone, Poly Ether Ketone Ketone, Polyurethane, metals such as stainless steel, titanium, titanium alloy, shape memory alloy, and any combinations of such metals and polymers.

According to a further feature of an embodiment of the present invention, the implant materials may include carbon fibers and/or glass fibers.

According to a further feature of an embodiment of the present invention, the implant includes further a locking arrangement to retain the implant in the fully deflected state, and wherein the locking arrangement includes elements selected from the group consisting of: cords, cables, strips, interconnections and snaps.

According to a further feature of an embodiment of the present invention, the implant includes further a locking arrangement to anchor the implant in the fully deflected state to the body, and wherein the locking arrangement includes elements selected from the group consisting of: cords, cables, strips, interconnections and snaps.

According to a further feature of an embodiment of the present invention, the locking arrangement is made primarily from material selected from the group consisting of: polymers such as Ultra High Molecular Weight Poly Ethylene, Poly Ether Ether Ketone, Poly Ether Ketone Ketone, metals such as stainless steel, titanium, titanium alloy, shape memory alloy, and any combinations of such metals and polymers.

According to a further feature of an embodiment of the present invention, the implants at least two segments may be opened horizontally in the axial plane.

According to a further feature of an embodiment of the present invention, the implants at least two segments may be opened vertically in the sagittal plane and may be used for vertebral augmentation.

According to a further feature of an embodiment of the present invention, the implants at least two segments may be opened simultaneously and/or sequentially in more than one plane.

According to a further feature of an embodiment of the present invention, a method for implanting interbody fusion implants is disclosed. The method includes the steps (a) providing an implant having a straightened insertion state for insertion into a body and a fully deflected loop state inside the body, the loop defining an enclosed volume, (b) providing a linkage for deflecting the implant from the straightened insertion state towards the fully deflected state inside the body, (c) providing at least one opening in the implant's deflected state allowing access to the enclosed volume, (d) filling the at least one enclosed volume with filling material for interbody fusion.

According to a further feature of an embodiment of the present invention, a method for implanting motion preservation implants is disclosed. The method includes the steps (a) providing an implant having a straightened insertion state for insertion into a body and a fully deflected loop state inside the body, the loop defining an enclosed volume, (b) providing a linkage for deflecting the implant from the straightened insertion state towards the fully deflected state inside the body, (c) providing at least one opening in the implant's deflected state allowing access to the enclosed volume, (d) filling the at least one enclosed volume with filling material for motion preservation.

There is also provided according to an embodiment of the present invention, a method comprising the steps of: (a) receiving an implant having a loop structure which assumes a straightened insertion state for insertion into a body and a deployed state inside the body, the deployed state of the loop at least partially defining an enclosed volume, the loop structure including at least one opening through a wall of the loop structure to allow access to the enclosed volume; (b) introducing the implant in the straightened insertion state into the body; (c) causing the implant to assume the deployed state within the body; and (d) introducing a filling material into the enclosed volume via the opening.

According to a further feature of an embodiment of the present invention, the implant is introduced into an intervertebral space, and wherein the filling material is chosen to induce fusion between adjacent vertebral bodies.

According to a further feature of an embodiment of the present invention, the implant is introduced into an intervertebral space, and wherein the filling material is chosen to allow motion preservation between adjacent vertebral bodies.

According to a further feature of an embodiment of the present invention, the implant is introduced into a vertebral body.

There is also provided according to an embodiment of the present invention, a method comprising the steps of (a) receiving an implant having a loop structure which assumes a straightened insertion state for insertion into a body and a deployed state inside the body, the deployed state of the loop at least partially defining an enclosed volume, the loop structure including at least one opening through a wall of the loop structure to allow access to the enclosed volume; (b) introducing the implant in the straightened insertion state into the body; and (c) causing the implant to transform progressively towards the deployed state within the body so as to distract adjacent tissue.

According to a further feature of an embodiment of the present invention, the implant is configured to expand while transforming towards the deployed state in at least two dimensions.

According to a further feature of an embodiment of the present invention, the implant is introduced into an intervertebral space for distracting between adjacent vertebral bodies.

According to a further feature of an embodiment of the present invention, the implant is introduced into a vertebral body for restoring a height of a vertebral body.

According to a further feature of an embodiment of the present invention, the implant is introduced into the body through a conduit which constrains the implant to the insertion state.

According to a further feature of an embodiment of the present invention, the method includes further the steps of providing elongated conduit for holding inside the conduit the straightened state implant and for inserting the straightened state implant to the body.

According to a further feature of an embodiment of the present invention, the method includes further the steps of providing elongated guide and loading on the tip of the guide and press-fitting into the body the straightened state implant.

According to a further feature of an embodiment of the present invention, the method includes further the steps of measuring the size of the evacuated disc space in preparation for implanting the implant and confirming that there is sufficient space for the implant to be successfully implanted in the evacuated disc space.

Additional features and advantages of the invention will become apparent from the following drawings and description.

BRIEF DESCRIPTION OF THE DRAWINGS

For a better understanding of the invention and to show how the same may be carried into effect, reference will now be made, purely by way of example, to the accompanying drawings in which like numerals designate corresponding elements or sections throughout.

With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice. In the accompanying drawings:

FIG. 3d illustrates the implant in its fully deflected state in the spine, according to embodiments of the present invention;

FIG. 4a-c illustrates an implant with fewer segments in straightened, partial and fully deflected states, according to embodiments of the present invention;

FIGS. 6a(1-2) illustrate an implant with different number of segments in each side in a straightened and a fully deflected state, according to embodiments of the present invention;

FIGS. 6b(1-3) illustrate the implant deployment using a tension element, according to embodiments of the present invention;

FIGS. 6c(1-3) illustrate the implant deployment using an internal tensioning element, according to embodiments of the present invention;

FIGS. 7b(1-3) illustrate the elliptical implant in straightened, partially deflected and fully deflected states, according to embodiments of the present invention;

FIGS. 7c(1-2) illustrate the elliptical implant in straightened and fully deflected states with two internal tensioning elements, according to embodiments of the present invention;

FIGS. 9a(1-2) illustrate a 3D implant in straightened and fully deflected state, according to embodiments of the present invention;

FIGS. 9b(1-2) illustrate the 3D implant in straightened and fully deflected state in lateral views in between two vertebrae, according to embodiments of the present invention;

FIG. 10b is a side view corresponding to the state of FIG. 10a.

DETAILED DESCRIPTION OF THE PREFERRED EMBODIMENTS

Figure 1:
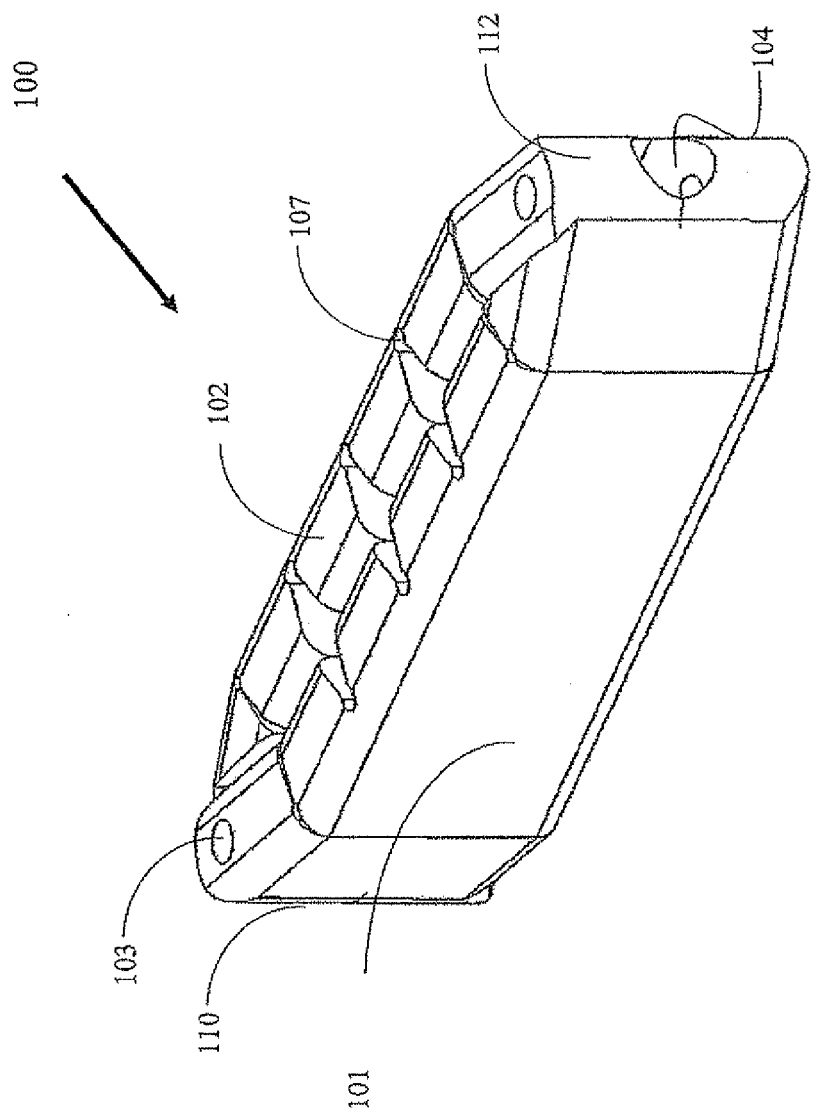
FIG. 1 illustrates an implant in a straightened state, according to embodiments of the present invention.

Certain embodiments of the present invention provide deflectable implants, systems and methods for implanting deflectable implants having a loop structure in a human or animal body. The loop structure is preferably pre-formed as a closed loop structure during delivery of the implant, but assumes a low-profile configuration folded on itself and/or straightened, to facilitate delivery via a minimally invasive procedure. In certain embodiments, the implant is arranged to open towards opposing sides of the axis defined by the direction of insertion, and may be symmetrical or asymmetrical about that axis, as will be exemplified below, thereby allowing the implant form and deployment sequence to be optimized for a range of different applications and approach directions.

In the context of the present description and claims, the word "loop" is used to refer to any structure in which following along the contiguous structure can lead back to the starting point while encircling at least one point lying outside the device. In certain cases, completion of the loop may be in the form of a sliding joint (as will be exemplified in FIG. 8 below). The word "loop" does not carry any implication of a circular or smooth shape, although such shapes are in certain cases preferred implementations of the loop structure when open.

The term "low profile" is used to refer to a configuration of a device in which at least one dimension of the device is significantly reduced, typically to less than 50% of the corresponding dimension of its deployed state, in order to facilitate delivery. In the present context, the low-profile configuration preferably has two transverse dimensions which are small compared to the direction of elongation, for easy delivery in a minimally invasive procedure, and the device opens up in one or two transverse dimensions when deployed.

Particularly preferred but non-limiting examples of implementations include intervertebral implants for supplementing, supporting or replacing an intervertebral disc as part of a fusion procedure or as a motion preserving implant, and intravertebral implants for supporting or restoring a vertebral body. The deflectable implants may include sequences of segments interconnected with effective hinges (such as conventional hinges or integral hinges) or may be formed with at least two elongated sides without clearly distinguished segments.

According to certain embodiments of the present invention, an implant that includes at least one sequence of segments, the sequence includes further at least two segments, more preferably at least three, and in many preferred cases four or more segments. The segments are interconnected at effective hinges, the sequence assuming a straightened or low curvature insertion state for insertion into the body, and being deflectable to a fully deflected state defined by abutment of abutment features of adjacent of the segments. Alternatively, the effective hinges may be configured to allow a range of angular motion beyond what is required to reach the fully open state. In the latter case, precise delineation of the desired final deployed state of the implant may be achieved by use of lateral tie elements, as will be described below. The implant preferably also includes a linkage, mechanically linked to at least part of at least one of the sequences of segments for deflecting the at least one sequence of segments from the insertion state towards the fully deflected state, wherein the at least one sequence is at least part of a loop structure assuming a low profile folded state with the at least one sequence in the insertion state, and wherein deflection of the at least one sequence towards the fully deflected state generates an open state of the loop structure.

According to certain embodiments of the present invention, a deflected implant may not have clearly distinct segments, but rather being formed from a single body of slotted or otherwise flexible material with at least first and second elongated sides interconnected at their proximal and distal ends, the at least first and second elongated interconnected sides assuming a straightened insertion state for insertion into a body, the at least first and second elongated interconnected sides being deflectable to a fully deflected loop inside the body, where the loop defines an enclosed volume with the upper and lower surfaces of the body. A linkage mechanically linked to at least part of at least one of the elongated interconnected sides, such as a tensioning element or a rod as two non limiting examples, may be used for deflecting the at least first and second elongated interconnected sides from the straightened insertion state towards the fully deflected loop inside the body.

According to certain embodiments of the present invention, an implant for interbody fusion is disclosed. The implant being deflectable to a fully deflected loop inside the body, where the loop defines an enclosed volume with the upper and lower surfaces of the bodies. The implant for interbody fusion further includes at least one opening in one or both of the elongated sides allowing access to the enclosed volume wherein the at least one opening is used to fill the enclosed volume in the fully deflected loop state with biocompatible filling materials for interbody fusion.

According to certain embodiments of the present invention, an implant for motion preservation is disclosed. The implant is deflectable to a fully deflected loop inside the body, where the loop defines an enclosed volume with the upper and lower surfaces of the body. The implant for interbody fusion further includes at least one opening in one or both of the elongated sides allowing access to the enclosed volume wherein the at least one opening is used to fill the enclosed volume in the fully deflected loop state with inert biocompatible filling materials applicable for motion preservation.

According to certain embodiments of the present invention, an implant system for implanting implants described herein above is disclosed. The implant system includes further an injector containing filling materials such as but not limited to biocompatible materials, bone grafts, bone chips, bone-growth enhancing agents for interbody fusion or inert filling materials, such as cement for interbody fusion or for stabilizing compression fractures, or other nucleus reinforcement or replacement material for motion preservation.

FIG. 1 illustrates an implant in a straightened state, according to embodiments of the present invention. Implant 100 includes at least one sequence of segments 102, with at least two segments, the segments being interconnected at effective hinges 107. Hinged interconnection is provided at one or both of the proximal and distal ends of the sequences of segments, allowing closing together of the two sequences of segments into low-profile closely adjacent positions when straightened, for convenient delivery in a minimally invasive operative procedure. The sequence of segments assumes a straightened or low curvature insertion state for insertion into the body as shown in FIG. 1. The two sequences of segments may be hingedly interconnected at both a distal end 110 and a proximal end 112 of each sequence. In other embodiments of the invention, the two sequences of segments are hingedly interconnected at one of a distal end 110 or a proximal end 112 of each sequence, preferably at the distal end 110, while completion of the loop at the other end is by some other form of interconnection, such as a sliding interconnection, as will be exemplified below with reference to FIG. 8.

A linkage (not shown in FIG. 1) is provided for deflecting the implant from the straightened insertion state towards the fully deflected state generating a loop structure in the body. In certain embodiments, the linkage is a tensioning element connected to the distal end 110 and threaded through an opening in the proximal end hinge 104. The tensioning element is used to reduce the distance between the distal and proximal ends of the implants' sequences.

An alternative set of non-limiting implementations of a linkage for deflecting the implant are arrangements for causing flexing of one or both segment sequences directly, such as an internal tensioning element as shown in FIG. 6B herein below. There may be a separate tensing element for each side (internal or external) or a single tensing element for both sides. In the case of two tensioning elements, each one may be activated separately or all may be activated simultaneously. The tensioning elements may be attached to the proximal end and to the distal end axels or to the individual segments or a combination. In certain embodiments of the present invention, the tensioning element may be a pull rod that is connected to the distal segments (in such a way that the pull rod does not interfere with the segment's movement) and extends through the proximal segments through an opening 104.

Actuation of a linkage for deflecting/opening the implant from its low-profile insertion state to its open deployed state is typically performed by operation of various actuating rocks) or cable(s) or string(s) or strip(s) extending along the length of a minimally invasive delivery system, such as a conduit, all as is well known in the art. The motion or force required for actuation may originate from a manually operable handle, or from an automated or semi-automated mechanical or electrical actuator. Details of these arrangements a within the capabilities of a person having ordinary skill in the relevant art, and do not per se constitute part of the present invention. For conciseness, such details are therefore not described herein in detail.

The tensioning elements may be fabricated from metal (including steel, shape memory alloy, titanium or other) or polymer rods, metal or plastic cables or similar or a combination. The tensioning elements may be removed from the implant or remain completely or partially attached to the implant after deployment. The tensioning element may have a locking mechanism to enable controlled attachment and separation from the implant. The tensioning elements may have a mechanism to maintain a tensed configuration of the fully deflected implant.

Alternatively, the implant may be deflected by employing the properties of memory shape material or other materials with suitable resilient properties. Such memory shape or otherwise resilient material may constitute at least part of the implant's sequence of segments. In these embodiments, no linkage or tensing element may be necessary.

Figure 2:
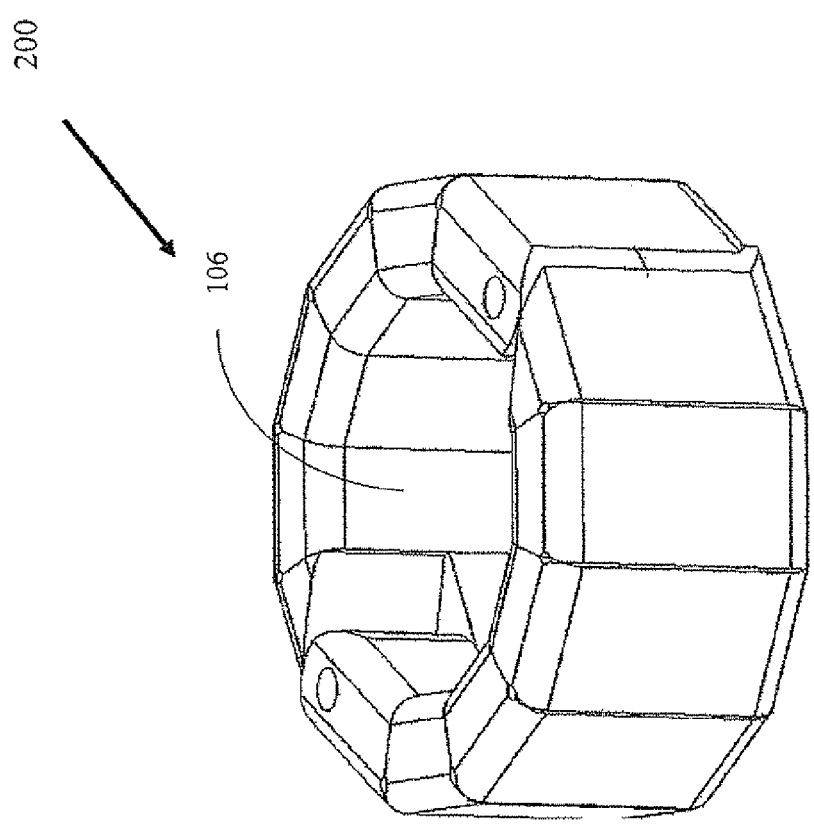
FIG. 2 illustrates the implant in a fully deflected state, according to embodiments of the present invention.

FIG. 2 illustrates the implant in a fully deflected state, according to embodiments of the present invention. When the tensing element is pulled relative to the proximal end, the implant is deflected to the fully deflected state 200 inside a body enclosing a volume 106 formed with the upper and the bottom surfaces of the body that may be for example the upper and lower endplates of vertebrae. Bone chips or bone enhancing agents or any other biological or other agent may be inserted into the enclosed volume 106. Optionally, there may be a window, a plurality of windows or similar opening in the fully deflected implant to facilitate insertion of filling materials into the enclosed volume 106.

Parenthetically, it should be noted that the term "enclosed volume" in the specification and claims refers to a volume which is encompassed on all sides in at least one plane, but does not necessarily imply closure above and below. In certain applications, the implants of the present invention are inserted between adjacent surfaces of tissue such that, together with the adjacent tissue surfaces, the enclosed volume becomes fully enclosed. Furthermore, the term "enclosed" does not rule out the presence of one or more opening through the enclosing structure, such as to allow filling of the enclosed volume through the wall of the implant, as will be discussed further herein.

According to certain embodiments of the present invention, the implant 100 may be deflected to its fully deflected state by linkage elements such as tensioning elements, inflation of balloons, by springs, by memory-shape material (such as Nitinol or similar materials), by turning a threaded rod, by a jacking mechanism, by injection of bone graft or other biologic material to promote fusion or by any other mechanical means. In other cases, the implant may be inherently resiliently biased to the deployed (open) state, and may temporarily be elastically deformed to the insertion state for deployment.

According to certain embodiments of the present invention, the implant 100 may be made of a polymer such as: Poly Ethylene, UHMWPE—Ultra High Molecular Weight Poly Ethylene, PEEK—Poly Ether Ether Ketone, Poly Ether Ketone Ketone, Poly Urethane as non limiting examples, or metal such as stainless steel, titanium, titanium alloy, shape memory alloy, as non limiting examples, or other material or a combination of such materials. The polymer materials may be reinforced with carbon fibers, glass fibers or similar filling materials known in the art.

According to certain embodiments of the present invention, the implant 100 may have a locking mechanism to retain the final fully deflected state. The locking mechanism may include a plurality of mechanisms that include cords, cables, strips, interconnections, snaps, or any other means known in the art, between each segment or a single mechanism for the entire implant or a combination. The locking mechanism may be fabricated from metal, including steel, shape memory alloy, titanium or other, or plastic or a combination. The locking mechanism may include a linkage or tensing element used to deflect the implant.

According to embodiments of the present invention, the implant may include a stabilizing arrangement to anchor the implant in the fully deflected state to the body. The locking arrangement may include a plurality of mechanisms that include cords, cables, strips, interconnections, snaps, ridges and any other means known in the art. The locking mechanism may be fabricated from metal, including steel, shape memory alloy, titanium or other, or plastic or a combination.

Figure 3A:
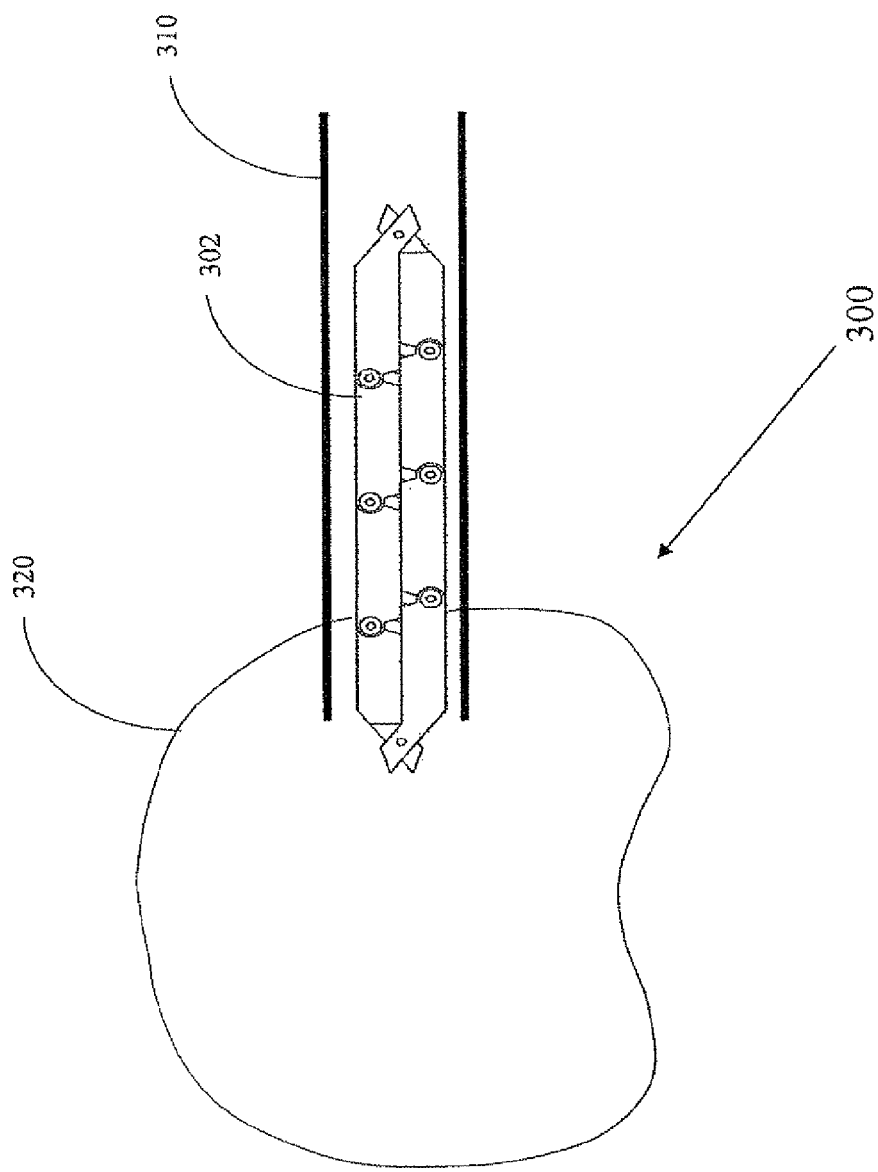
FIG. 3a illustrates an implant partially deployed, according to embodiments of the present invention.

FIG. 3a illustrates an implant partially deployed, according to embodiments of the present invention. The implant in a straightened state 302 is shown inside a conduit 310 ready for deployment in an evacuated disc space in a vertebra 320. The implant 302 may be inserted into the disc space 320 using a conduit 310 acting as a working channel. Alternatively, according to certain embodiments of the present invention, the implant may also be inserted into the disc space by being loaded on a tip of a guide and press-fit into the disc space. The implant 302 may have various heights and diameters to ideally accommodate the disc anatomy. In certain embodiments of the inventions, the implants may be designed as lordotic or kyphotic to accommodate the spine anatomy.

Figure 3B:
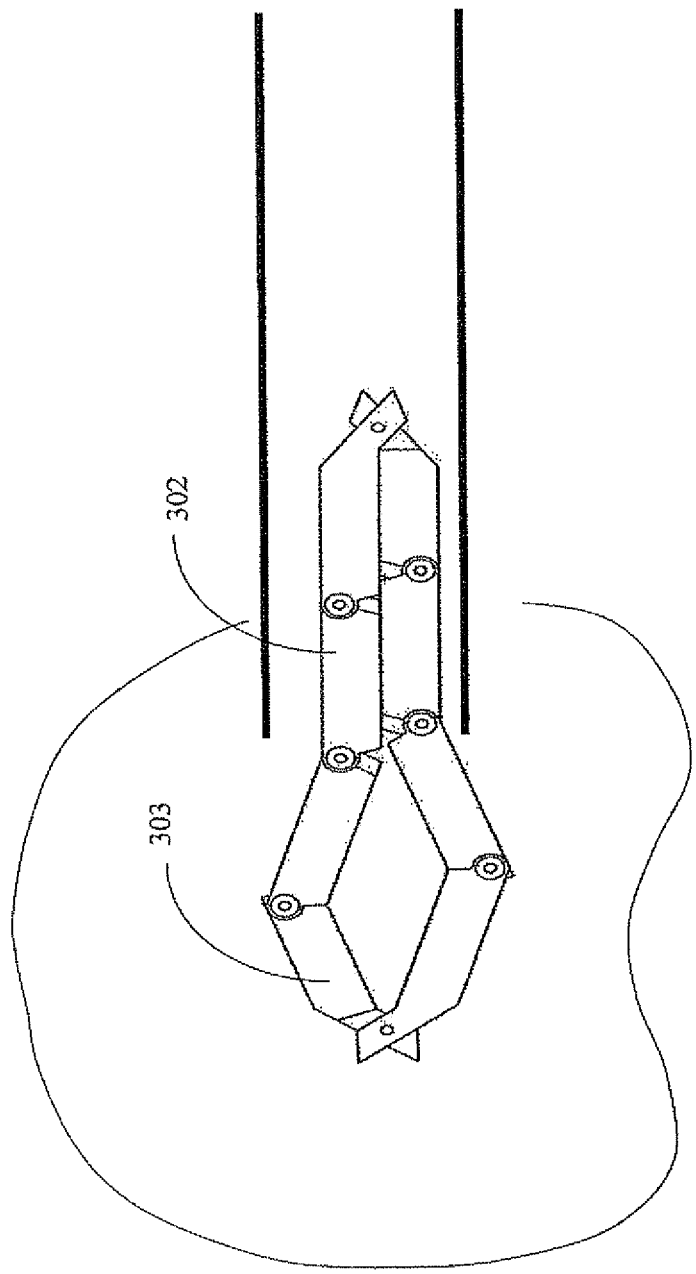
FIG. 3b illustrates the implant partially deflected in the spine, according to embodiments of the present invention.

FIG. 3b illustrates the implant partially deflected in a spine, according to embodiments of the present invention. A proximal part of the implant 302 is still in a straightened state inside a conduit 310 while a distal part is deployed and partially deflected in the evacuated disc space in a vertebra 320.

Figure 3C:
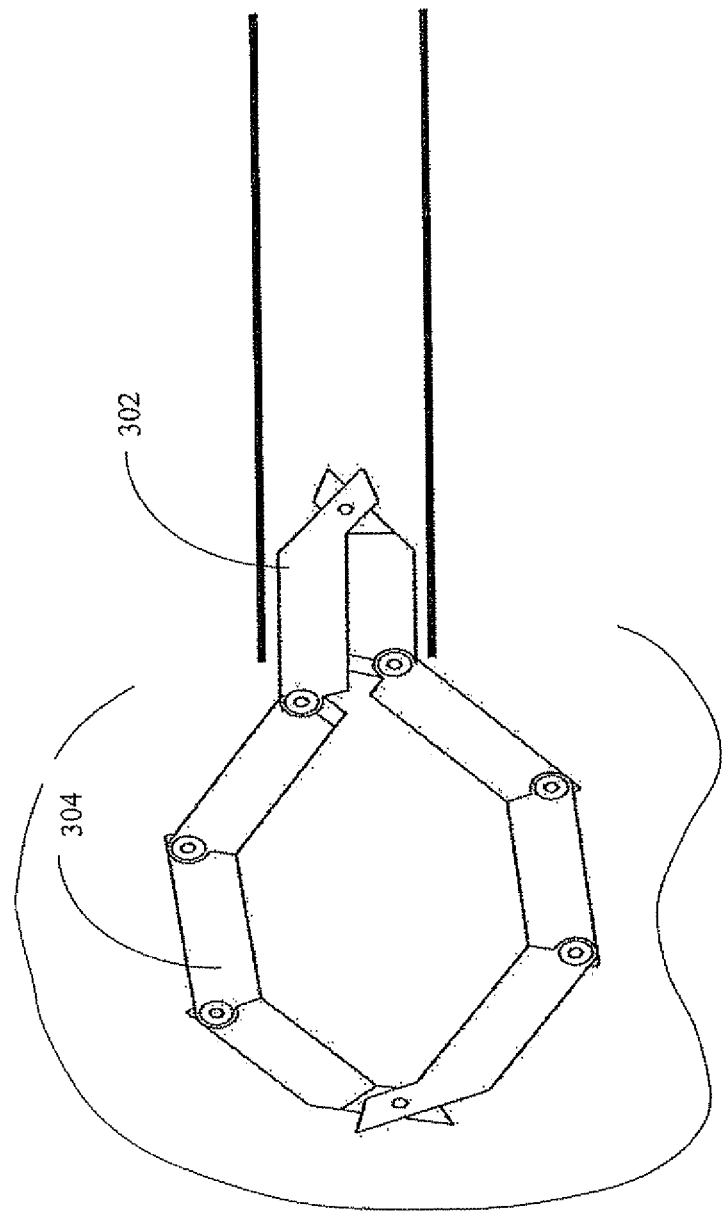
FIG. 3c illustrates the implant further deflected in the spine, according to embodiments of the present invention.

FIG. 3c illustrates the implant further deflected in the spine, according to embodiments of the present invention. A smaller part of the implant 302 with fewer segments is still in a straightened state inside a conduit 310 and a larger distal part 304 is deployed and deflected in the evacuated disc space in the vertebra 320.

FIG. 3d illustrates the implant in its fully deflected state in the spine, according to embodiments of the present invention. Implant 308 is fully deflected in the spine 320. The implant in its fully deflected state encloses a volume 330 that may be filled with various filling materials for interbody fusion or other materials for motion preservation or for stabilizing a vertebra.

Figure 4A:
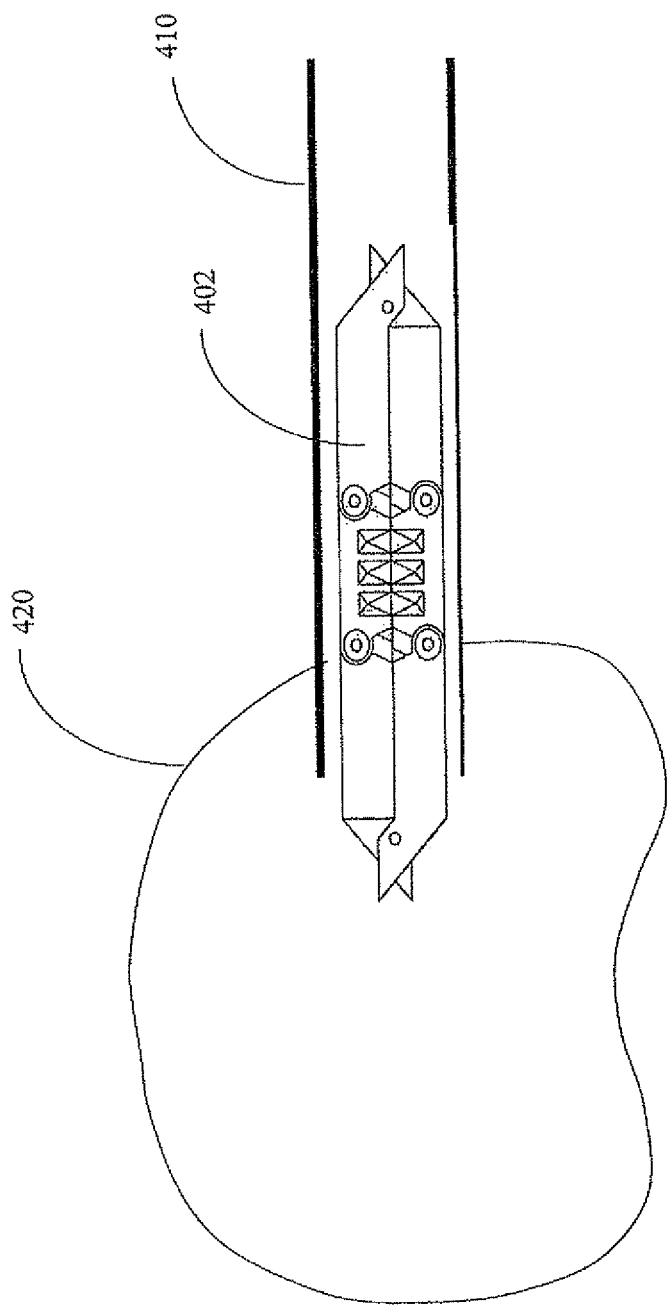
Figure 4C:
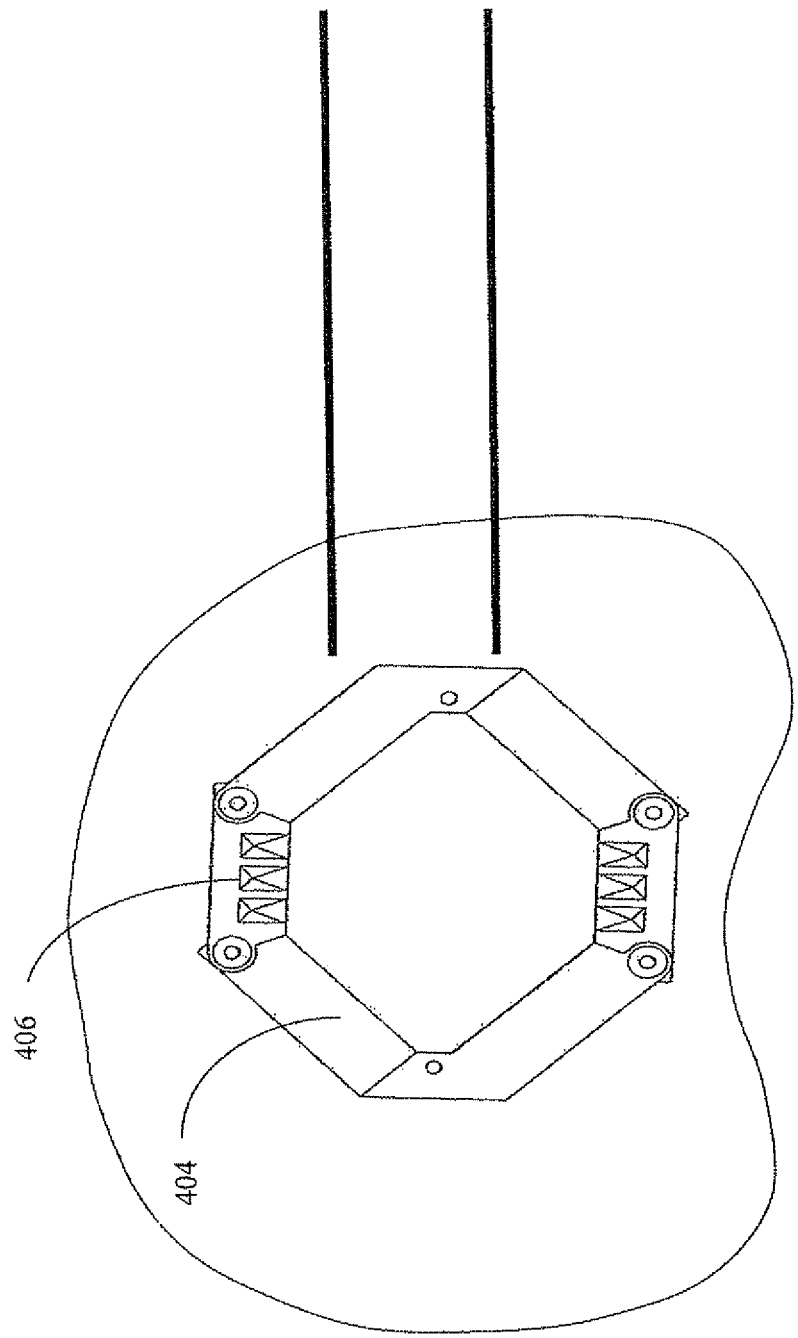

FIG. 4a-c illustrates an implant with fewer segments in straightened, partial and fully deflected states, according to embodiments of the present invention. FIG. 4a illustrates an implant with fewer segments in a straightened state 402 inside a conduit 410 ready for deployment in an evacuated disc space 420 in a spine. FIG. 4b illustrates the proximal part of the implant 402 still in a straightened state inside the conduit while the distal part 403 is deployed and partially deflected in the evacuated disc space in a vertebra. FIG. 4c illustrates the implant 404 fully deflected in the vertebra. In certain cases, implant 404 has projections 406 on the top and bottom surfaces. Projections 406 may be rigid or flexible and may fold flat onto the sides or into recesses. The projections 406 may be effective to scrape the upper and bottom vertebral endplates and/or help to anchor the implant in position relative to the adjacent tissue.

Figure 4D:
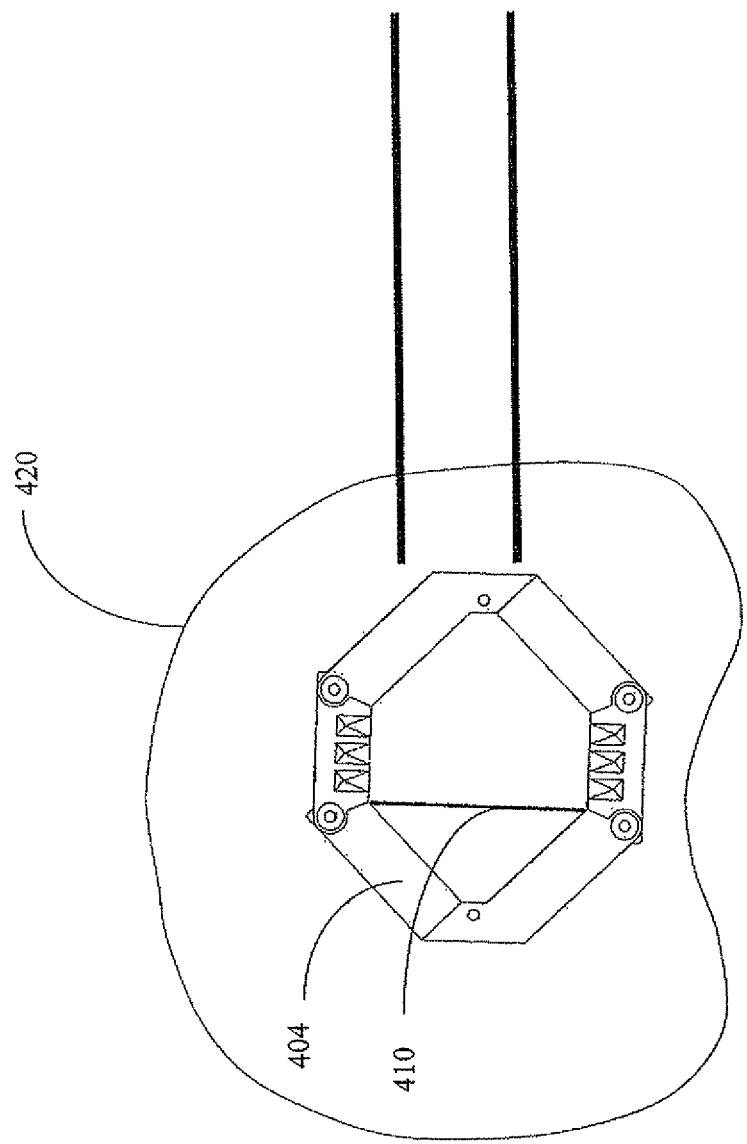
FIG. 4d illustrates the implant in its fully deflected state in the spine with a tension element used to fix the maximal width, according to embodiments of the present invention.

FIG. 4d illustrates the implant in its fully deflected state in the disc space with a transversely deployed tie element 410 used to fix the maximal width, according to embodiments of the present invention. Implant 404 is shown in its fully deflected state while tie element 410 is used to fix the maximal width of the implant inside the vertebra 420. The use of one or more lateral tie element serves to define the fully open state of the implant, typically as an alternative to using a limited range of motion of the hinges between segments to define the fully open configuration. This allows the implant to assume intermediate states during opening of the implant where the hinges between segments temporarily assume angles which are beyond the range of flexing allowed in the fully deployed state, such as is shown in FIG. 4B. In certain embodiments, a plurality of lateral tie elements may be provided spread along the length of the implant (not shown).

Figure 5A:
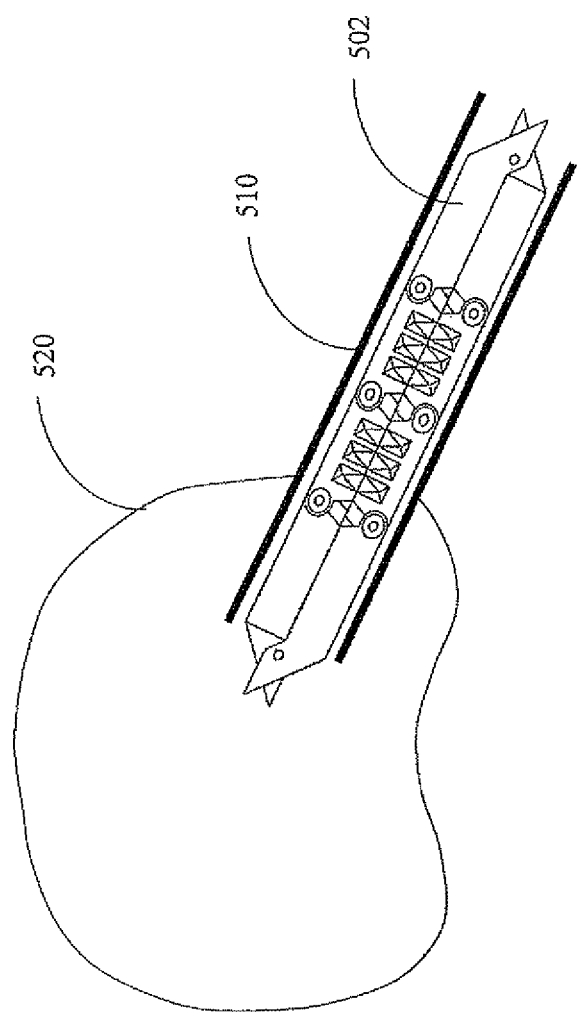
FIG. 5a-c illustrates an implant in straightened, partial and fully deflected states with final double ring shape, according to embodiments of the present invention.
Figure 5B:
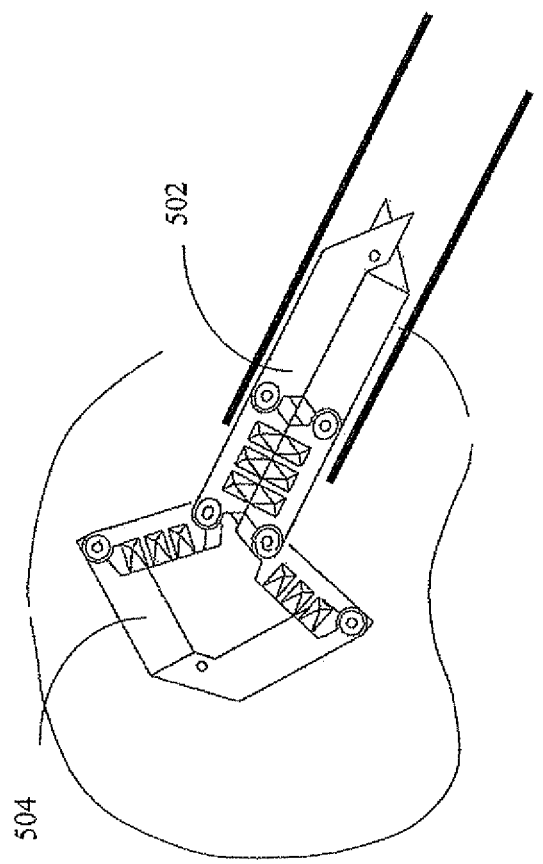
Figure 5C:
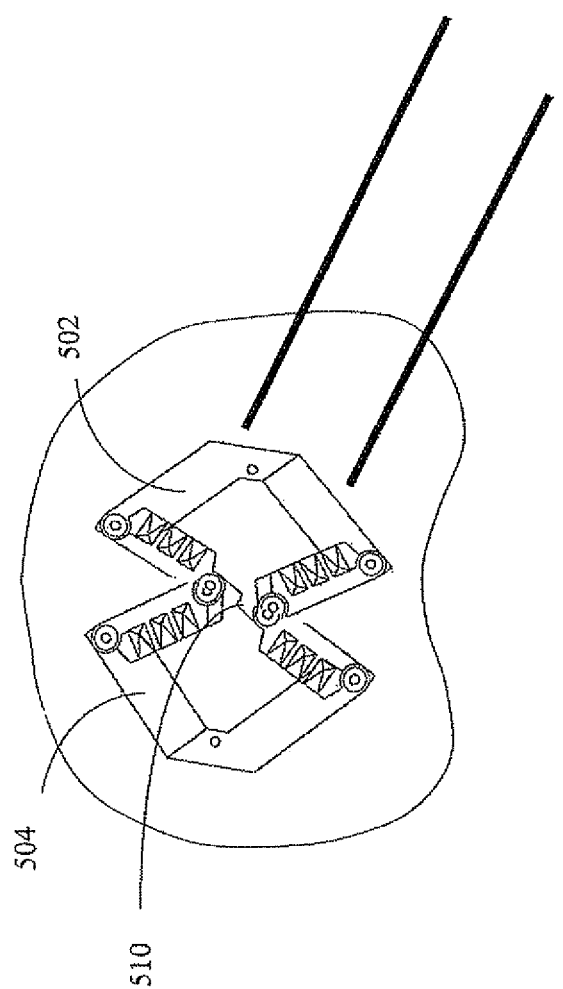

FIG. 5a-c illustrates an implant in straightened, partial and fully deflected states with final "double ring" or "figure-eight" shape, according to embodiments of the present invention. FIG. 5a illustrates a double ring implant in a straightened state 502 inside a conduit 510 ready for deployment in an evacuated disc space in a spine 520. FIG. 5b illustrates the proximal part of the implant 502 still in a straightened state inside the conduit while the distal part 504 is deployed and partially deflected in the evacuated disc space in the spine. FIG. 5c illustrates the implant fully deflected in the disc space with a double ring 502 and 504 shape. Tensioning element 510 is used to fix the medial part width of the implant as shown in the figure. It should be noted that the double loop or double ring is so called in view of the general overall form of the implant as illustrated, but that the narrow central region is not necessarily connected from side to side. Thus, this embodiment may also be viewed as an example of a loop insert which has a recess or concavity on at least one side, and which has a medial region which has a local minimum in a transverse dimension of the deployed implant.

FIGS. 6a(1-2) illustrate an implant with different number of segments in each side in a straightened and a fully deflected state, according to embodiments of the present invention. The asymmetric implant in a straightened state 602 is shown in FIG. 6a(1) in the left side and the fully deflected state 604 in FIG. 6a(2) in the right side. The asymmetric implant has 2 segments on the first side and 5 smaller segments on the second side. The sizes and the hinges of the asymmetric implant are designed such that in the fully deflected state 604 a smooth loop structure is obtained.

FIGS. 6b(1-3) illustrate the implant deployment using a tension element, according to embodiments of the present invention. FIG. 6b(1) illustrates the implant in its straitened state 602 in the right upper side with tensioning element 610. FIG. 6b(2) illustrates the implant in partially deflected state 604 with tensioning element 610 connected to the distal part 608 and is partially drawn back through the proximal part 609 such that the distance between the proximal 609 and the distal 608 ends is reduced. FIG. 6b(3) illustrates the implant in fully deflected state 606 in the left bottom side of the figure with tensioning element 610 connected to the distal part 608 and is drawn further back such that the distance between the proximal and the distal ends is further reduced in the fully deflected state. The tensioning elements may be removed from the implant or remain attached to the implant after deployment FIGS. 6c(1-3) illustrate the implant deployment using internal tensioning element, according to embodiments of the present invention. The asymmetric implant is shown in its straitened in FIG. 6c(1), partially deflected in FIG. 6c(2) and fully deflected states in FIG. 6c(3). The internal tensioning element threads the implant segments sequentially. The internal tensioning element is anchored to one side of the proximal part 614, threads through the distal part 616 and threads further through the second side of the proximal part 618. Pulling back tensioning element 620 reduces the distance between the ends of the distal and the proximal parts and deflects the implant to its fully deflected state as shown on the bottom left side of FIG. 6c. In other embodiments, at least two internal tensioning elements may be used, each of them dedicated to each of at least two sequences of segments.

Figure 7A:
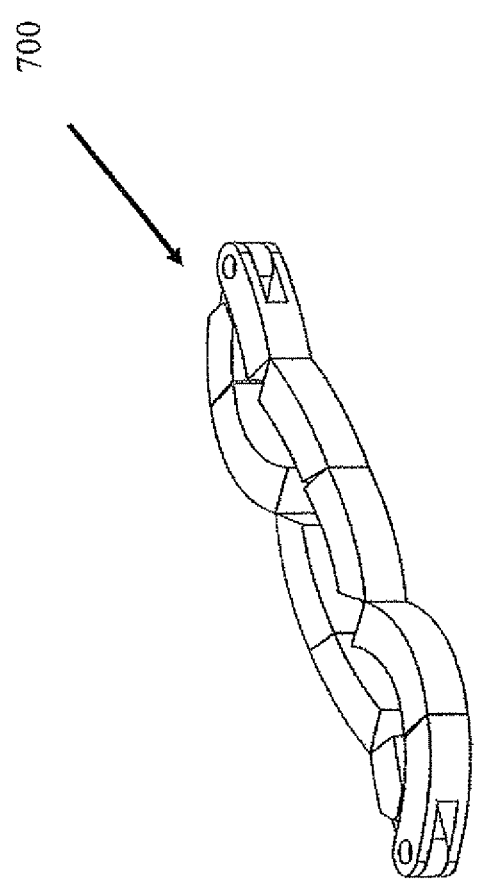
FIG. 7a illustrates an elliptical shape implant in a straightened state, according to embodiments of the present invention.

FIG. 7a illustrates an elliptical shape implant in a straightened state, according to embodiments of the present invention. Implant 700 is shown in its straightened state and is another asymmetric implant according to embodiments of the present invention where the two sequences of segments between the proximal and distal ends are not a mirror reflection of each other.

FIGS. 7b(1-3) illustrate the elliptical implant in straightened, partially deflected and fully deflected states, according to embodiments of the present invention. FIG. 7b(1) illustrates the elliptical implant straightened state 702 inside the conduit, FIG. 7b(2) illustrates the partially deflected state 704 when partially deployed and FIG. 7b(3) illustrates the fully deflected state 706 when fully deployed. The elliptical implant as shown here deploys as an off-axis ellipse, i.e., where neither the major nor the minor axis of the ellipse is aligned with the axis defined by the deployment direction. The ability to deploy an asymmetric implant, or a symmetric implant with an orientation offset relative to the deployment direction, is particularly valuable for allowing appropriate deployment of inserts during procedures with a range of different access directions.

FIGS. 7c(1-2) illustrates the elliptical implant in straightened FIG. 7c(1) and fully deflected FIG. 7c(2) states with two internal tensioning elements, according to embodiments of the present invention. Two internal tensioning elements 718 and 719 are anchored to two sides of the distal end segments 708 and 709. The two tensioning elements are threaded through the segments sequences from each side of the implant. The two tensioning elements may extend along one or along both sides of the elongated sequences of segments to allow selective deflection of the implant towards the implant fully deflected state. The two tensioning elements may be pulled simultaneously or one after the other deflecting the implant to the fully elliptical deflected state shown on the bottom left in FIG. 7c(2).

Figure 8:
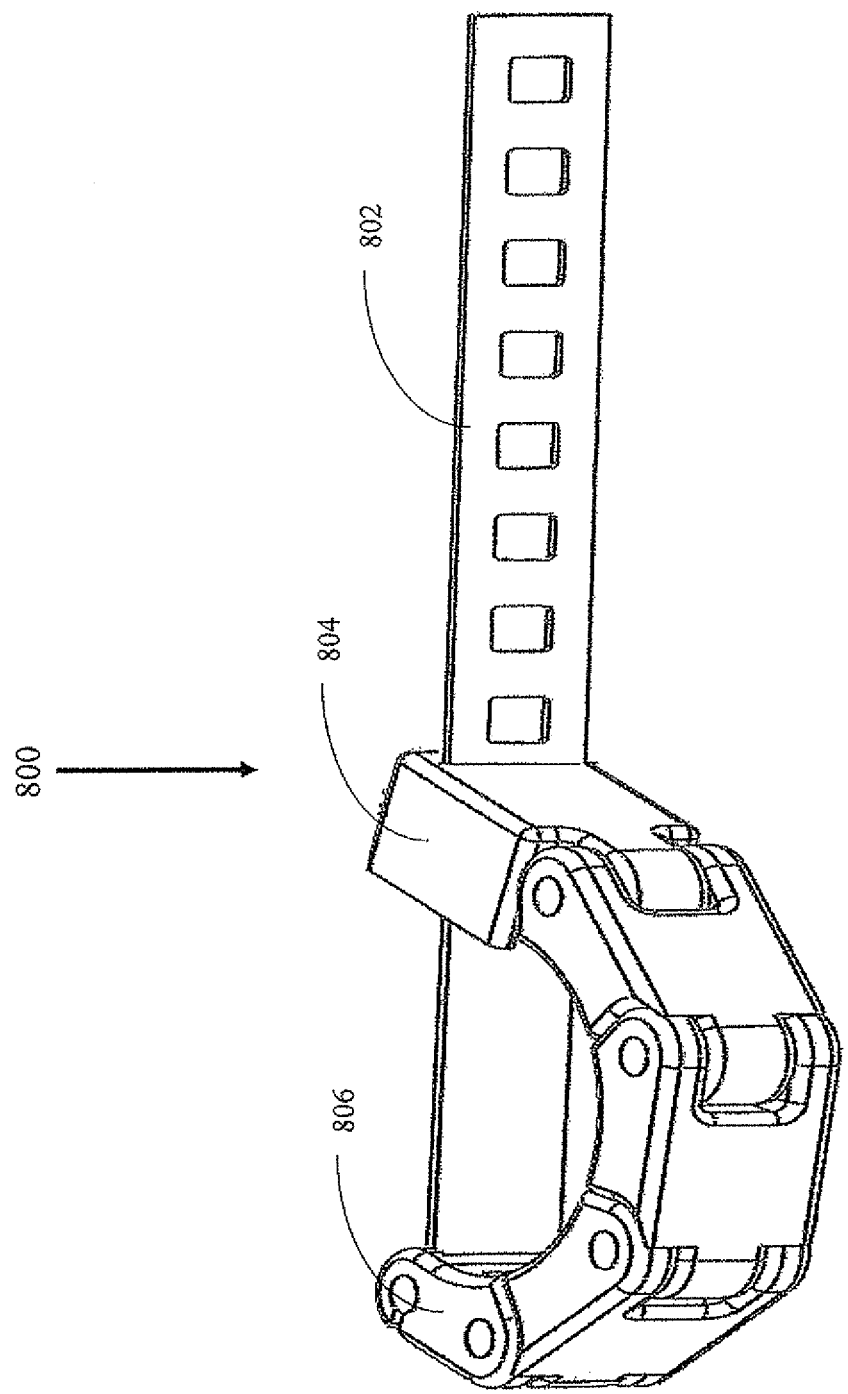
FIG. 8 illustrates a D-shape implant in fully deflected states, according to embodiments of the present invention.

FIG. 8 illustrates a D shape implant 800 in a fully deflected state, according to embodiments of the present invention. The D-shape implant is another asymmetric implant according to embodiments of the present invention. The D-shape implant has one flat segment 802, defining a direction of elongation, on a first side and a sequence of segments 804, 806 interconnected with hinges on the second side. The flat segment as shown here is straight, and is formed without internal hinges such that a transformation of said loop from said low profile folded state to said open state occurs without internal deflection of said second side of said loop. The D-shape implant has a straightened insertion state with low cross section and a fully deflected state as shown in FIG. 8. As in all of the above embodiments, transformation of the loop from its low profile folded state to its open state effects expansion of the implant as a whole transverse to the direction of elongation and in a single plane containing the direction of elongation. In certain embodiments, the sequence of segments is deflected by applying longitudinal pressure with a pusher (not shown) to the proximal part 804 of the sequence, which is shown here a being slidingly interconnected to flat segment 802, thus causing a relative movement between the sequence's segments and the flat segment without the need for any linkage or tensing element.

FIGS. 9a(1-2) illustrate a three dimensional (3D) implant in straightened and fully deflected states, according to embodiments of the present invention. FIG. 941) shows the 3D implant in its straightened insertion state 940 and FIG. 9a(2) shows the 3D implant in its fully deflected state 950. The 3D implant may be opened horizontally 905, in the body axial plane or vertically 906 in the body sagittal plane or at any other angle. Furthermore, the 3D implant may be opened in more than one plane simultaneously or sequentially. In the 3D case the implant has more than two sides (901, 902, 903 and 904 for example) forming a three dimensional shape.

FIGS. 9b(1-2) illustrate the 3D implant in straightened and fully deflected state in lateral views in between two vertebrae, according to embodiments of the present invention. FIG. 9b(1) shows the upper vertebra 910 bottom vertebra 912 and the 3D implant 914 positioned in between the two vertebrae in its straightened insertion state 940. FIG. 9b(2) shows the upper vertebra 910 bottom vertebra 912 and the 3D implant 916 positioned in between the two vertebrae in its fully deflected state 950. The deflected implant 916 increases the height between the two vertebrae in the sagittal plane and can be used to fix compression fracture of discs by restoring the height between the two vertebrae thus the deflected implant 916 may be used for vertebral augmentation. The 3D implant illustrated in FIGS. 9a-b is merely a non limiting example of a 3D implant according to embodiments of the present invention. Other geometries with larger contact surfaces with the two vertebrae for example may be designed and are in the scope of the present invention.

Another application of a 3D implant is for vertebral augmentation with or without the addition of a stabilizing agent such as cement for treating degenerative or trauma vertebra fracture cases.

According to embodiments of the present invention, the fully deflected state of the implants may be toroidal polyhedrons, ring toroids, elliptical toroids and multi-ring toroids as shown in the various drawings which are merely non limiting examples of deflected implants that are in the scope of the present invention and where other deflected implants may be designed by persons skilled in the art according to embodiments of the present invention.

Turning finally to FIGS. 10a-10d, it should be noted that, where hinged interconnection is used between the elongated elements, the hinge axis need not be perpendicular to the length of the implant. By way of one non-limiting example, FIGS. 10a-10d illustrate an example of an implant 1000 in which a hinge axis 1002a and 1002b for folding of the implant extends along a diameter or length of the deployed implant.

Figure 10A:
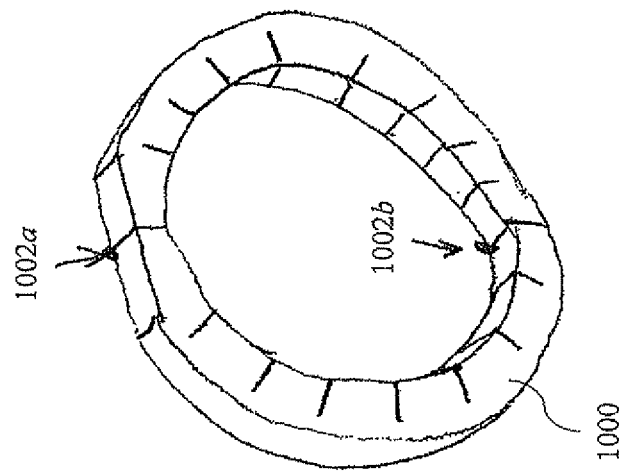
FIGS. 10a, 10c and 10d are schematic isometric views illustrating an implant according to a further embodiment of the present invention, the implant being shown in its straightened delivery state, an intermediate curved state and a fully open state, respectively.
Figure 10B:
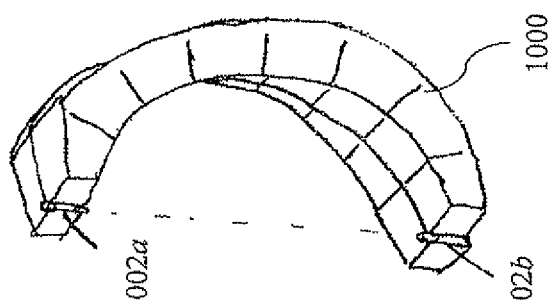
Figure 10C:
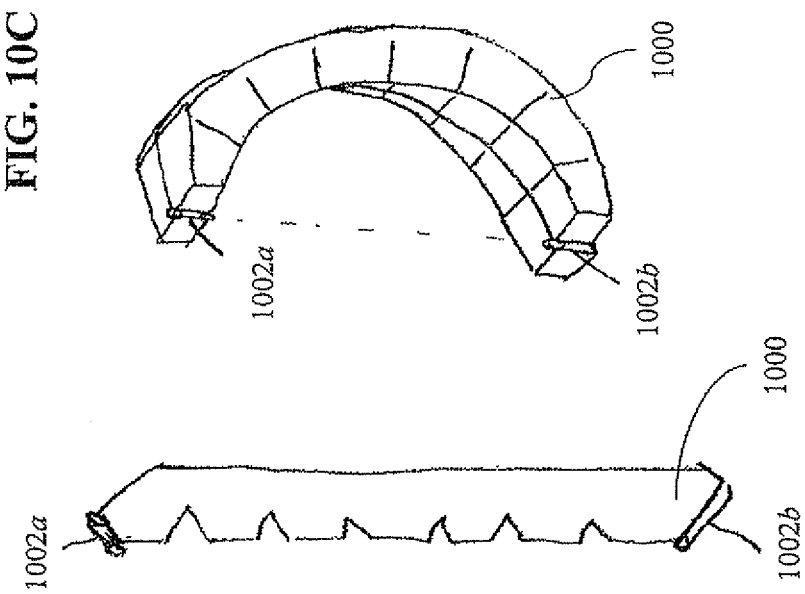
Figure 10D:
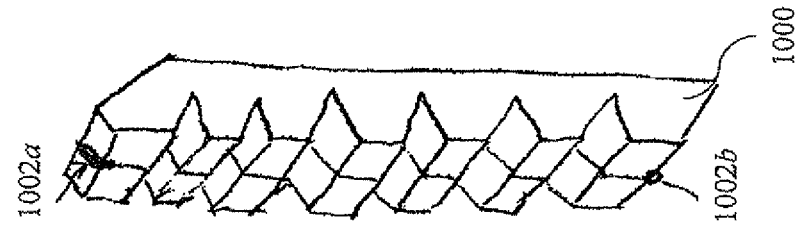

In this case, in the straightened state of FIGS. 10a and 10b, hinge axes 1002a and 1002b are not aligned, and the implant is locked against opening. Only when the implant is deflected to the state of FIG. 10c do the two hinge axes come into alignment, allowing the pivotal opening of the two halves of the implant to assume the open configuration of FIG. 10d. Here too, all the options of various actuating linkages or use of inherent resilient biasing are applicable.

In summary, deflectable implants described above may be used for interbody fusion, for motion preservation and for vertebral augmentation. The deflectable implants may be used as intervertebral implants or/and intravertebral implants. Other spinal and non-spinal applications of such implants are also envisaged.

Advantageously, embodiments of the deflectable implants described above have low cross section in their straightened insertion state allowing them to be inserted through a small orifice in the skin.

Another advantage of certain embodiments of the deflectable implants described above is that their fully deflected state may fill the intervertebral disc space replacing a sick disc tissue.

Another advantage of certain embodiments of the deflectable implants described above is that their fully deflected state may have at least one opening that may be filled with bone grafts and other biocompatible materials for interbody fusion.

Another advantage of certain embodiments of the deflectable implants described above is that their fully deflected state may have at least one opening that may be filled with inert materials for motion preservation.

Another advantage of certain embodiments of the deflectable implants described above is that their fully deflected state in more than one plane and particularly in the sagittal plane may be used for vertebral augmentation.

It is appreciated that certain features of the invention, which are, for clarity, described in the context of separate embodiments, may also be provided in combination in a single embodiment. Conversely, various features of the invention which are, for brevity, described in the context of a single embodiment, may also be provided separately or in any suitable sub-combination.

Unless otherwise defined, all technical and scientific terms used herein have the same meanings as are commonly understood by one of ordinary skill in the art to which this invention belongs. Although methods similar or equivalent to those described herein can be used in the practice or testing of the present invention, suitable methods are described herein.

All publications, patent applications, patents, and other references mentioned herein are incorporated by reference in their entirety. In case of conflict, the patent specification, including definitions, will prevail. In addition, the materials, methods, and examples are illustrative only and not intended to be limiting.

It will be appreciated by persons skilled in the art that the present invention is not limited to what has been particularly shown and described hereinabove. Rather the scope of the present invention is defined by the appended claims and includes both combinations and sub-combinations of the various features described hereinabove as well as variations and modifications thereof, which would occur to persons skilled in the art upon reading the foregoing description.

What is claimed is:

1. An implant comprising:
 a first side of a loop comprising a sequence of segments extending between a proximal end and a distal end, said sequence comprising at least three segments, said at least three segments being interconnected at effective hinges, said sequence assuming a straightened or low curvature insertion state in which said sequence exhibits a first length from said proximal end to said distal end for insertion into the body, said sequence being deflectable to a deflected state in which said sequence exhibits a second length from said proximal end to said distal end, smaller than said first length; and
 a second side of a loop comprising at least one segment and having a direction of elongation, said first and second sides being hingedly interconnected at at least one of said distal end and said proximal end to form at least part of a loop assuming a low profile folded state in which said first side and said second side are brought together and said sequence is in said insertion state, and assuming an open state in which said sequence is deflected towards said deflected state and said loop at least partially defines an enclosed volume, wherein at least one of a proximal extremity and a distal extremity of said implant is formed by a hinge joint between a segment of said first side and a segment of said second side, and wherein said second side of said loop is formed without internal hinges such that a transformation of said loop from said low profile folded state to said open state occurs without internal deflection of said second side of said loop, and wherein transformation of said loop from said low profile folded state to said open state effects expansion of the implant as a whole transverse to said direction of elongation and in a single plane containing said direction of elongation.

2. The implant of claim 1, further comprising a linkage mechanically linked to at least part of said sequence of segments for deflecting said sequence of segments from said insertion state towards said deflected state.

3. The implant of claim 1, further comprising a pusher for applying longitudinal pressure to said proximal end so as to selectively reduce a distance between said distal and proximal ends of said sequence.

4. The implant of claim 1, wherein said implant further comprises at least one opening in said sequence of segments to allow access to the enclosed volume in said loop.

5. The implant of claim 1, further comprising a locking arrangement to retain said implant in said deflected state, and wherein said locking arrangement includes at least one element selected from the group consisting of: cords, cables, strips, interconnections and snaps.

6. The implant of claim 1, wherein said second side is implemented as an elongated segment hingedly interconnected with said sequence of segments at a distal end of said sequence, said sequence of segments being slidingly interconnected with said elongated segment at the proximal end of the sequence of segments, said sequence of segments and said elongated segment together defining said loop.

7. The implant of claim 6, wherein said open state of the implant is D-shaped.

8. The implant of claim 6, wherein said sliding interconnection is configured such that longitudinal pressure applied to a proximal part of the sequence of segments generates relative movement between the sequence's segments and the elongated segment, thereby deflecting the sequence of segments to form the open state of said loop.

9. An implant system comprising the implant of claim 1, and further comprising an elongated conduit for inserting said implant in said straightened insertion state into the body.

10. An implant system comprising the implant of claim 1, and further comprising an injector containing filling material selected from the group consisting of: biocompatible materials, bone grafts, bone chips, bone-growth enhancing agents for interbody fusion and inert filling materials such as cements for motion preservation.

11. An implant comprising:
a first side of a loop comprising a sequence of segments extending between a proximal end and a distal end, said sequence comprising at least three segments, said at least three segments being interconnected at effective hinges, said sequence assuming a straightened or low curvature insertion state in which said sequence exhibits a first length from said proximal end to said distal end for insertion into the body, said sequence being deflectable to a deflected state in which said sequence exhibits a second length from said proximal end to said distal end, smaller than said first length; and a second side of a loop comprising at least one segment, said first and second sides being hingedly interconnected at at least one of said distal end and said proximal end to form at least part of a loop assuming a low profile folded state in which said first side and said second side are brought together and said sequence is in said insertion state, and assuming an open state in which said sequence is deflected towards said deflected state and said loop at least partially defines an enclosed volume, wherein at least one of a proximal extremity and a distal extremity of said implant is formed by a hinge joint between a segment of said first side and a segment of said second side, and wherein said second side of said loop has fewer segments than said first side of said loop, and wherein said second side of said loop is straight between said proximal end and said distal end, thereby defining a direction of elongation, wherein transformation of said loop from said low profile folded state to said open state effects expansion of the implant as a whole transverse to said direction of elongation and in a single plane containing said direction of elongation.

* * * * *